United States Patent
Nilsson et al.

(10) Patent No.: US 12,228,480 B2
(45) Date of Patent: Feb. 18, 2025

(54) BIOLOGICAL SAMPLE PREPARATION USING ELECTRIC FIELDS

(71) Applicant: Revvity Health Sciences, Inc., Waltham, MA (US)

(72) Inventors: Michael Nilsson, Mendon, MA (US); Erhard Ralf Schoenbrunner, Charlestown, MA (US)

(73) Assignee: Revvity Health Sciences, Inc., Waltham, MA (US)

( * ) Notice: Subject to any disclaimer, the term of this patent is extended or adjusted under 35 U.S.C. 154(b) by 869 days.

(21) Appl. No.: 16/696,269

(22) Filed: Nov. 26, 2019

(65) Prior Publication Data

US 2020/0173890 A1 Jun. 4, 2020

Related U.S. Application Data

(60) Provisional application No. 62/773,927, filed on Nov. 30, 2018.

(51) Int. Cl.
   *G01N 1/28* (2006.01)
   *G01N 1/40* (2006.01)
   (Continued)

(52) U.S. Cl.
   CPC .............. *G01N 1/2813* (2013.01); *G01N 1/40* (2013.01); *G01N 27/3275* (2013.01);
   (Continued)

(58) Field of Classification Search
   CPC .... G01N 1/2813; G01N 1/40; G01N 27/3275; G01N 27/4145; G01N 33/4836;
   (Continued)

(56) References Cited

U.S. PATENT DOCUMENTS 4,294,677 A * 10/1981 Sakagami ................. C25B 7/00
                                                     204/489
4,747,918 A * 5/1988 Wassenberg ....... G01N 27/4473
                                                     436/515
(Continued)

FOREIGN PATENT DOCUMENTS

CN         106350512 A  *  1/2017

OTHER PUBLICATIONS

Shaw et al., The use of carrier RNA to enhance DNA extraction from microfluidic-based silica monoliths, Analytica Chimica Acta, 2009, 652, 231-233 (Year: 2009).*

(Continued)

*Primary Examiner* — Luan V Van
*Assistant Examiner* — Shizhi Qian
(74) *Attorney, Agent, or Firm* — Seed IP Law Group LLP

(57) ABSTRACT

Systems and methods use electric fields to separate bioanalytes from a substrate comprising a biological sample. Biological material, especially blood samples, are sometimes dried onto absorbent substrates. By applying an electric field across the substrate, or a portion thereof, bioanalytes from the sample are attracted to a conductor having a positive or negative charge, depending on the charges carried by the bioanalytes. The electric field can be created using two conductors in circuit with a power source, and the substrate may be positioned between the conductors.

31 Claims, 19 Drawing Sheets

(51) Int. Cl.
  G01N 27/327    (2006.01)
  G01N 27/414    (2006.01)
  G01N 33/483    (2006.01)
  G01N 33/487    (2006.01)
(52) U.S. Cl.
  CPC ..... *G01N 27/4145* (2013.01); *G01N 33/4836* (2013.01); *G01N 33/48721* (2013.01); *G01N 2001/2826* (2013.01); *G01N 2001/4038* (2013.01)
(58) Field of Classification Search
  CPC ..... G01N 33/48721; G01N 2001/2826; G01N 2001/4038; B01D 57/02; B01L 2300/0645; B01L 2300/069; B01L 2400/0421; B01L 3/5023
  See application file for complete search history.

(56) References Cited

U.S. PATENT DOCUMENTS

| | | | | |
|---|---|---|---|---|
| 5,415,758 | A * | 5/1995 | Comeau | G01N 27/4473 204/464 |
| 5,532,166 | A * | 7/1996 | Ma | G01N 27/44721 436/175 |
| 2003/0135030 | A1 | 7/2003 | Guttman et al. | |
| 2009/0301883 | A1 * | 12/2009 | Chung | G01N 27/44721 204/600 |
| 2010/0133098 | A1 * | 6/2010 | Hafeman | G01N 27/44756 204/403.01 |
| 2012/0277118 | A1 | 11/2012 | Bhatia et al. | |
| 2013/0248366 | A1 | 9/2013 | Haswell et al. | |
| 2015/0353989 | A1 * | 12/2015 | Fraser | C12Q 1/6806 506/40 |
| 2015/0362459 | A1 * | 12/2015 | Chung | G01N 1/40 204/547 |
| 2016/0281078 | A1 * | 9/2016 | Fabis | C12Q 1/6874 |
| 2017/0240882 | A1 * | 8/2017 | Abrams | C12N 15/1017 |
| 2021/0009715 | A1 * | 1/2021 | Benesova | A61K 51/0482 |

OTHER PUBLICATIONS

Matsubara et al., Microchamber array based DNA quantification and specific sequence detection from a single copy via PCR in nanoliter volumes Biosensors and Bioelectronics, 2005, 20, 1482-1490 (Year: 2005).*

Zheng et al., English translation of CN106350512A, 2017 (Year: 2017).*

Kishore et al., Optimization of DNA extraction from low-yield and degraded samples using the BioRob EZ1 and BioRob M48, J. Forensic Sci., 2006, 51(5), 1055-1061 (Year: 2006).*

Goldstein et al., In Vitro antimicrobial activity of a new antibiotic, MDL 62,879 (GE2270 A), Antimicrobial Agents and Chemotherapy, 1993, 37(4), 741-745 (Year: 1993).*

Higgins et al., Evaluation of carrier RNA and low volume demineralization for recovery of nuclear DNA from human teeth, Forensic Sci Med Pathol, 2014, 10, 56-61 (Year: 2014).*

Adam et al., "Recoveries of Phenylalanine from Two Sets of Dried-Blood-Spot References Materials: Prediction from Hematocrit Spot vol. and Paper Matrix," *Clinical Chemistry* 46(1):126-128, 2000.

Baker et al., "Development of a routine newborn screening protocol for severe combined immunodeficiency," *J Allergy Clin Immunol* 124(3):522-527, 2009.

Borte et al., "Neonatal screening for severe primary immunodeficiency diseases using high-throughput triplex real-time PCR," *Blood* 119(11):2252-2555, 2012.

Cao et al., "Effectiveness of qPCR permutations, internal controls and dilution as means for minimizing the impact of inhibition while measuring Enterococcus in environmental waters," *Journal of Applied Microbiology* 113:66-75, 2012.

Cavanaugh et al., "Direct PCR amplication of forensic touch and other challenging DNA samples: A review," *Forensic Science International: Genetics* 32:40-49, 2018.

Cecco et al., "Eddy Current Testing: Manual on Eddy Current Method," Atomic Energy of Canada Limited, CM-P00067661, 1981.

Chan et al., "Development of population-based newborn screening for severe combined immunodeficiency," *J Allergy Clin Immonul* 115(2):391-398, 2005.

Cossu, "Genetics of SCID," *Italian Journal of Pediatrics* 36(76):1-17, 2010.

Demirev, "Dried Blood Spots: Analysis and Applications," *Anal. Chem.* 85(2):779-789, 2013.

Edwards et al., "Polymerase chain reaction compared with concurrent viral cultures for rapid identification of human immunodeficiency virus infection among high-risk infants and children," *The Journal of Pediatrics* 115(2):200-203, 1989.

Ellison et al., "Routes to improving the reliability of low level DNA analysis using real-time PCR," *BMC Biotechnology* 6:33, 2006.

Gaillard et al., "Avoiding DNA loss and denaturation upon storage in plastic microtubes," Institut Jacques Monod, Paris, France, pp. 1-6, No. date.

Gan et al., "A Filter Paper-Based Microdevice for Low-Cost, Rapid, and Automated DNA Extraction and Amplification from Diverse Sample Types," *Lab on a Chip, Accepted Manuscript*, 14:3719-3728, 2014.

Gerstel-Thompson et al., "High-Throughput Multiplexed T-Cell-Receptor Excision Circle Quantitative PCR Assay with Internal Controls for Detection of Severe Combined Immunodeficiency in Population-Based Newborn Screening," *Clinical Chemistry* 56(9):1466-1474, 2010.

Guthrie et al., "A Simple Phenylalanine Method for Detecting Phenylketonuria in Large Populations of Newborn Infants," *Pediatrics* 32(3):338-343, 1963.

Hale et al., "Identification of an infant with severe combined immunodeficiency by newborn screening," *Journal of Allergy and Clinical Immunology* 126(5):1073-1074, 2010.

Hue et al., "Extraction of Human Genomic DNA from Dried Blood Spots and Hair Roots," *International Journal of Bioscience, Biochemistry, and Bioinformatics* 2(1):21-26, 2012.

Kadjo et al., "Evaluation of Amount of Blood in Dry Blood Spots: Ring-Disk Electrode Conductometry," *Analytical Chemistry* 88:6531-6537, 2016.

King et al., "A quantitative approach to detect and overcome PCR inhibition in ancient DNA extracts," *BioTechniques* 47(5):941-949, 2009.

Lang et al., "Comparison of manual and automated DNA purification for measuring TREC in dried blood spot (DBS) samples with qPCR," *Journal of Immunological Methods* 384:118-127, 2012.

Lang et al., "Measuring the TREC ratio in dried blood spot samples: Intra- and inter-filter paper cards reproducibility," *Journal of Immunological Methods* 389(1-2):1-8, 2013.

Leaist et al., "Interdiffusion of acids and bases. HCl and NaOH in aqueous solution," *Can. J. Chem.* 64:1007-1011, 1986. (6 pages).

Li et al., "Electroporation on microchips: the harmful effects of pH changes and scaling down," *Nature: Scientific Reports* 5:1-11, 2015.

Punwani et al., "Cellular Calibrators to Quantitate T Cell Receptor Excision Circles (TRECs) in Clincal Samples," *Mol Genet Metab.* 107(3):586-591, 2012.

Rajatileka et al., "Isolation of human genomic DNA for genetic analysis from premature neonates: a comparison between newborn dried blood spots, whole blood and umbilical cord tissue," *BMC Genetics* 14(105):1-9, 2013.

Routes et al., "Statewide Newborn Screening for Severe T-Cell Lymphopenia," *JAMA* 302(22):2465-2470, 2009.

Saavedra-Matiz et al., "Cost-Effective and Scalable DNA Extraction Method from Dried Blood Spots," *Clincal Chemistry* 59(7):1045-1051, 2013.

Shaik et al., "Single Lysis-Salting Out Method of Genomic DNA Extraction From Dried Blood Spots," *Journal of Clinical Laboratory Analysis* 30:1009-1012, 2016.

(56) References Cited

OTHER PUBLICATIONS

Shaw et al., "The use of carrier RNA to enhance DNA extraction from microfluidic-based silica monoliths," *Analytica Chimica Acta* 652:231-233, 2009.

Van Zelm et al., "PID comes full circle: applications of V(D)J recombination excision circles in research, diagnostics and newborn screening of primary immunodeficiency disorders," *Frontiers in Immunology* 2(12):1-9, 2011.

Wilson, "Inhibition and Facilitation of Nucleic Acid Amplification," *Applied and Environmental Microbiology* 63(10):3741-3751, 1997.

* cited by examiner

| SAMPLE NAME | CONCENTRATION (ng/μl) |
|---|---|
| DBS IN BUFFER ALONE (5 MINUTES) | 0.43±0.31 |
| ELECTRIC PROTOCOL: 10 mM, 25V, 300s | 2.28±0.82 |
| LYSIS PROTOCOL | 3.12±0.59 |

BIOLOGICAL SAMPLE PREPARATION USING ELECTRIC FIELDS

BACKGROUND

Technical Field

The technology described herein relates to the separation of a biological sample contained on a substrate from the substrate, for example, separation of dried blood contained on a filter paper substrate from the filter paper substrate.

Description of the Related Art

Dried blood spot ("DBS") bio-sampling is a well-known technique for collecting and storing blood samples for analytical testing. In general, DBS specimens are collected by applying a few drops of blood onto an absorbent paper material, such as filter paper. For screening of newborns, for example, the blood is traditionally obtained via a finger, heel, or toe prick, or from cord blood, and then spotted onto the filter paper. Once the paper has dried for several hours, it is stored in a plastic bag and can be kept at ambient temperature. This bio-sampling technique provides an easy way to collect, store, and ship blood samples in a stable format without refrigeration.

To utilize a DBS sample in a laboratory analysis, a small disc of the saturated paper is separated from the sheet using a hole punch. Then, the separated disc is placed in a solution to elute the blood out of the disc. This step often requires 8-10 hours. The solution used to elute out the blood from the disc is typically a phosphate buffered saline containing a surfactant and emulsifier (such as polysorbate 80) and sodium azide. Many additional washing steps are typically required to isolate the desired components of the sample.

BRIEF SUMMARY

The present technology uses electric fields to separate bioanalytes from a biological sample contained on a substrate. According to a first example of the technology, a method for separating bioanalytes comprises: submerging at least a portion of the substrate in a buffer solution; bringing a first electrical conductor into contact with a buffer solution; bringing a second electrical conductor into contact with the buffer solution; creating a difference in electric potential energy between the first and second electrical conductors; and collecting separated bioanalytes from at least one of the first and second electrical conductors. In some examples, the method further comprises separating the first and second electrical conductors in the buffer solution; and positioning the portion of the sample storage medium between the first and second electrical conductors.

In some examples, the step of creating a difference in electric potential energy between the first and second electrical conductors comprises applying a voltage in a circuit connected to the conductors such that the first electrical conductor has a positive electrical charge and the second electrical conductor has a negative electrical charge. In some examples, the step of applying a voltage comprises the steps of: identifying a first type of bioanalyte to be collected; determining a first amount of voltage and a first period of time, wherein at least one of the first amount of voltage and the first period of time is determined based at least in part on the particular first type of bioanalytes identified; and applying the determined first amount of voltage to the first electrical conductor for the determined first period of time.

In some examples, the step of applying a voltage further comprises the steps of: identifying a second type of bioanalyte to be collected, the second type of bioanalyte to be collected being different than the first type of bioanalyte to be collected; determining a second amount of voltage and a second period of time, wherein at least one of the second amount of voltage and the second period of time is determined based at least in part on the particular second type of bioanalyte identified, wherein the second amount of voltage is different than the first amount of voltage, or the second period of time is different than the first amount of time, or both; and applying the determined second amount of voltage to the first electrical conductor for the determined second period of time. In some examples, at least one of the voltage applied and a period of time over which the voltage is applied is adjustable.

In some examples, the step of submerging at least a portion of a substrate containing a blood sample in a buffer solution comprises the steps of: separating the portion from the substrate using a punch, wherein the portion includes a blood sample to be analyzed; and submerging the portion in the buffer solution. In some examples, the substrate comprises a filter paper.

In some examples, the step of collecting separated bioanalytes further comprises the steps of: removing the first electrical conductor from the buffer solution; inserting the first electrical conductor into a material collection container; and reducing or eliminating the difference in electric potential energy between the first and second electrical conductors. In some examples, the step of collecting separated material further comprises the steps of: removing the second electrical conductor from the buffer solution; removing the portion of the substrate from the buffer solution; and reducing or eliminating the difference in electric potential energy between the first and second electrical conductors. In some examples, the step of collecting the separated bioanalytes further comprises the steps of: removing the portion of substrate from the buffer solution; removing the buffer solution from contact with the first and second electrical conductors; and reducing or eliminating the difference in electrical potential energy between the first and second electrical conductors.

The first electrical conductor may be a positive electrode, the second electrical conductor may be a negative electrode, and a side of the substrate spotted with the biological sample may face toward the positive electrode. Methods may further comprise treating a container holding the buffer solution with carrier RNA prior to filling the container with the buffer solution. Methods may further comprise adding bovine serum albumin to the buffer solution. A width of a gap between the first electrical conductor and the second electrical conductor may be greater than 0.05 cm and less than 0.2 cm. The buffer solution may include potassium hydroxide at a concentration greater than 5 mM and less than 20 mM. Creating a difference in electric potential energy between the first and second electrical conductors may include creating a voltage of greater than 10 V and less than 50 V. Creating a difference in electric potential energy between the first and second electrical conductors may include creating a difference in electric potential energy between the first and second electrical conductors for a period of time that is greater than 30 seconds and less than 300 seconds. Methods may further comprise heating the substrate to a temperature greater than 40° C. and less than 80° C. Heating the substrate may include heating the substrate for a period of time greater than one minute and less than six minutes.

According to a second example of the technology, a system for separating bioanalytes from a sample contained on a substrate comprises a first electrical conductor, a second electrical conductor, a process chamber, a source of electric power, at least one processor, at least one computer-readable medium, and software stored in the computer-readable medium and programmed to execute on the at least one processor. The process chamber is adapted to contain an amount of buffer solution, adapted to be coupled with both the first and second electrical conductors, and adapted to receive at least a portion of a substrate. The chamber is arranged such that the portion is disposed between the first and second electrical conductors. The source of electric power is coupled to the first and second electrical conductors for creating a difference in electrical potential energy between the first and second electrical conductors. The software controls the source of electric power to apply a voltage in a circuit connected to the first and second conductors so that the first conductor has a positive charge and the second conductor has a negative charge. The software also controls the source of electric power to reduce or eliminate the applied voltage so that bioanalytes separated from the substrate can be collected from the first electrical conductor.

In some examples, the system further comprises a material collection chamber and a motor coupled to the first electrical conductor and adapted to move the first electrical conductor into and out of the process chamber. The software controls the motor to move the electrical conductor out of the process chamber and into the material collection chamber before the applied voltage is reduced or eliminated.

In some examples, the system further comprises a motor coupled to the second electrical conductor and adapted to move the second electrical conductor into and out of the process chamber; and a sample removal device adapted to remove the portion of substrate from the process chamber. The software controls the motor to move the second electrical conductor out of the process chamber before the applied voltage is reduced or eliminated and controls the sample removal device to remove the portion of substrate from the process chamber before the applied voltage is reduced or eliminated.

In some examples, the software further controls the source of electric power to apply a first amount of voltage in a circuit connected to the first and second electrical conductors for a first period of time in order to attract a first type of bioanalyte to the first electrical conductor; and controls the source of electric power to apply a second amount of voltage in a circuit connected to the first and second electrical conductors for a second period of time in order to attract a second type of bioanalyte to the first electrical conductor. The second amount of voltage is different than the first amount of voltage or the second period of time is different than the first amount of time, or both.

In some examples, the process chamber is adapted to receive a portion of a filter paper, the portion having been removed from the filter paper by a hole punch and containing a blood sample to be analyzed. In some examples, the process chamber and the first and second electrical conductors are joined and comprise an electroporation cuvette.

According to a third example of the present technology, a method for separating bioanalytes from a sample contained on a substrate is provided. The method comprises: submerging at least a portion of the substrate in a buffer solution; contacting the buffer solution with a first electrical conductor and a second electrical conductor; identifying a first type of bioanalyte to be collected; determining a first amount of voltage and a first period of time, wherein at least one of the first amount of voltage and the first period of time is determined based at least in part on the particular first type of bioanalyte identified; and applying the determined first amount of voltage to the first electrical conductor for the determined first period of time.

In some examples, the method further comprises identifying a second type of bioanalyte to be collected, the second type of bioanalyte to be collected being different than the first type of bioanalyte to be collected; determining a second amount of voltage and a second period of time, wherein at least one of the second amount of voltage and the second period of time is determined based at least in part on the particular second type of bioanalyte identified, wherein the second amount of voltage is different than the first amount of voltage, or the second period of time is different than the first amount of time, or both; and applying the determined second amount of voltage to the first electrical conductor for the determined second period of time.

In some examples, the method further comprises the steps of: removing the first electrical conductor from the buffer solution; inserting the first electrical conductor into a material collection container; and reducing or eliminating the difference in electric potential energy between the first and second electrical conductors. In some examples, the method further comprises the steps of removing the second electrical conductor from the buffer solution; removing the portion of the substrate from the buffer solution; and reducing or eliminating the difference in electric potential energy between the first and second electrical conductors. In some examples, the method further comprises the steps of removing the portion of substrate from the buffer solution; removing the buffer solution from contact with the first and second electrical conductors; reducing or eliminating the difference in electrical potential energy between the first and second electrical conductors.

In some examples, either one or both of the first amount of difference in electric potential energy or the first period of time is selected to attract deoxyribonucleic acid to the first electrical conductor; and either one or both of the second amount of difference in electric potential energy or the second period of time is selected to attract ribonucleic acid to the first electrical conductor.

Other aspects of the technology described herein and its particular features will become more apparent from consideration of the following drawings and accompanying detailed description.

DETAILED DESCRIPTION

The present technology involves systems and methods for separating bioanalytes from biological samples stored on substrates using electric fields. Examples of the technology include systems and methods for separating bioanalytes from blood samples dried on paper substrates ("dried blood spots" or "DBS"). The technology is well suited for use with other biological samples containing nucleic acid, generally in the form of deoxyribonucleic acid (DNA) and/or ribonucleic acid (RNA).

Figure 1:
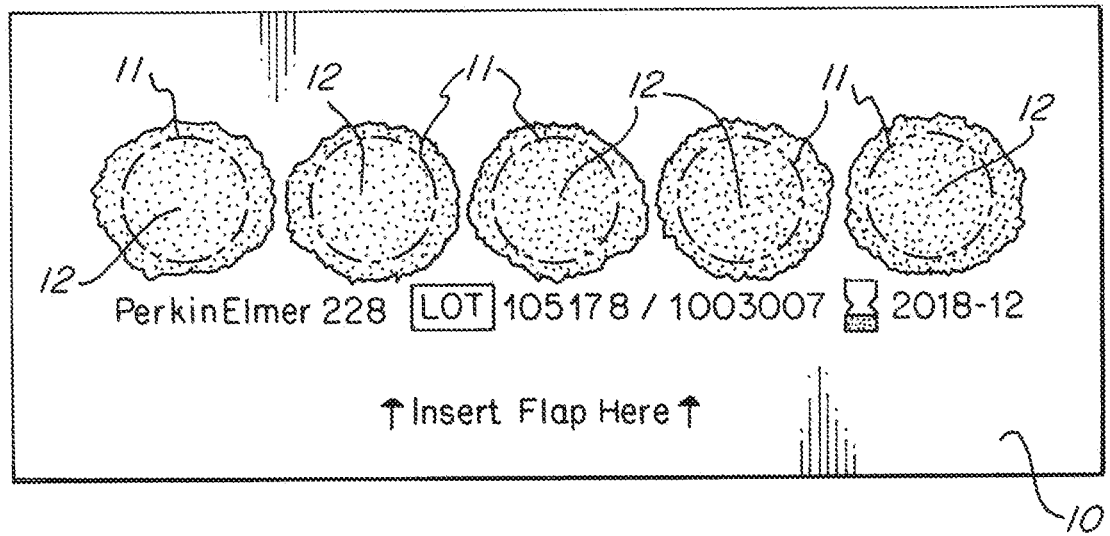
FIG. 1 shows a substrate the form of a card containing dried blood spots.

FIG. 1 shows an example of a dried blood spot card 10. The card 10 has five dotted rings 11 printed on it, which are intended to mark the placement of blood drops from an individual. The card 10 is made of an absorbent filter paper, and each sample ring will hold roughly 75-80 μl of blood sample. FIG. 1 shows 5 sample spots 12. Once the blood samples have dried on the card 10, the card can be stored in an air-tight plastic bag or container.

Figure 2:
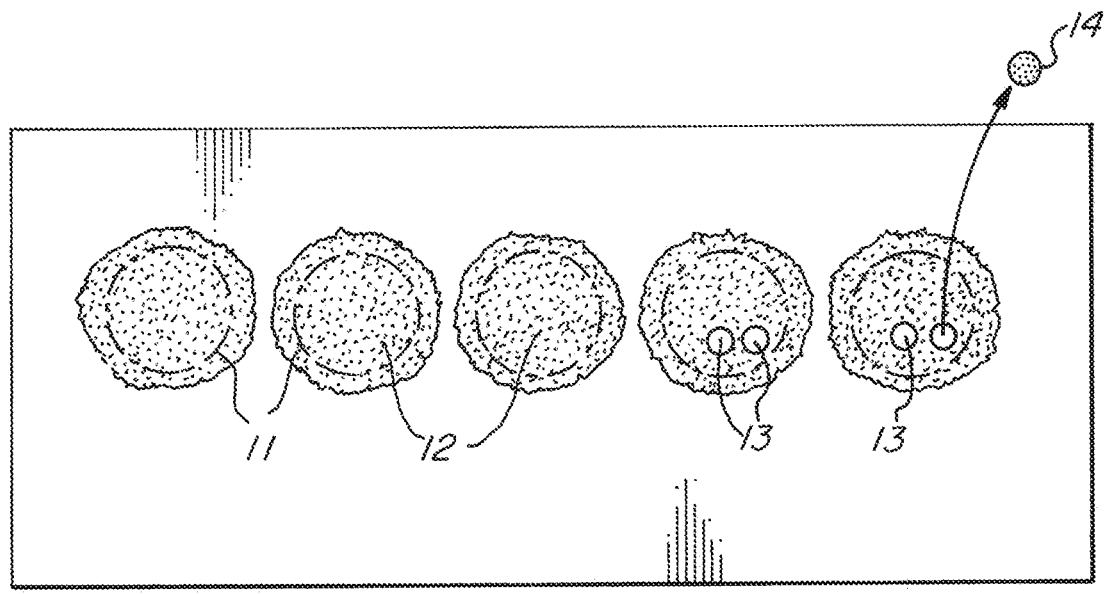
FIG. 2 shows the medium of FIG. 1 with sample portions removed.

FIG. 2 shows the card 10 with holes 13 in the sample spots 12. The holes 13 are the result of a hole punch removing a portion of the card containing a blood sample. A portion 14 containing a blood sample is also shown. As will be apparent to those of skill in the art, a single card 10 can provide numerous sample portions 14 to enable many different tests and analyses to be performed on the blood of an individual.

Figure 3:
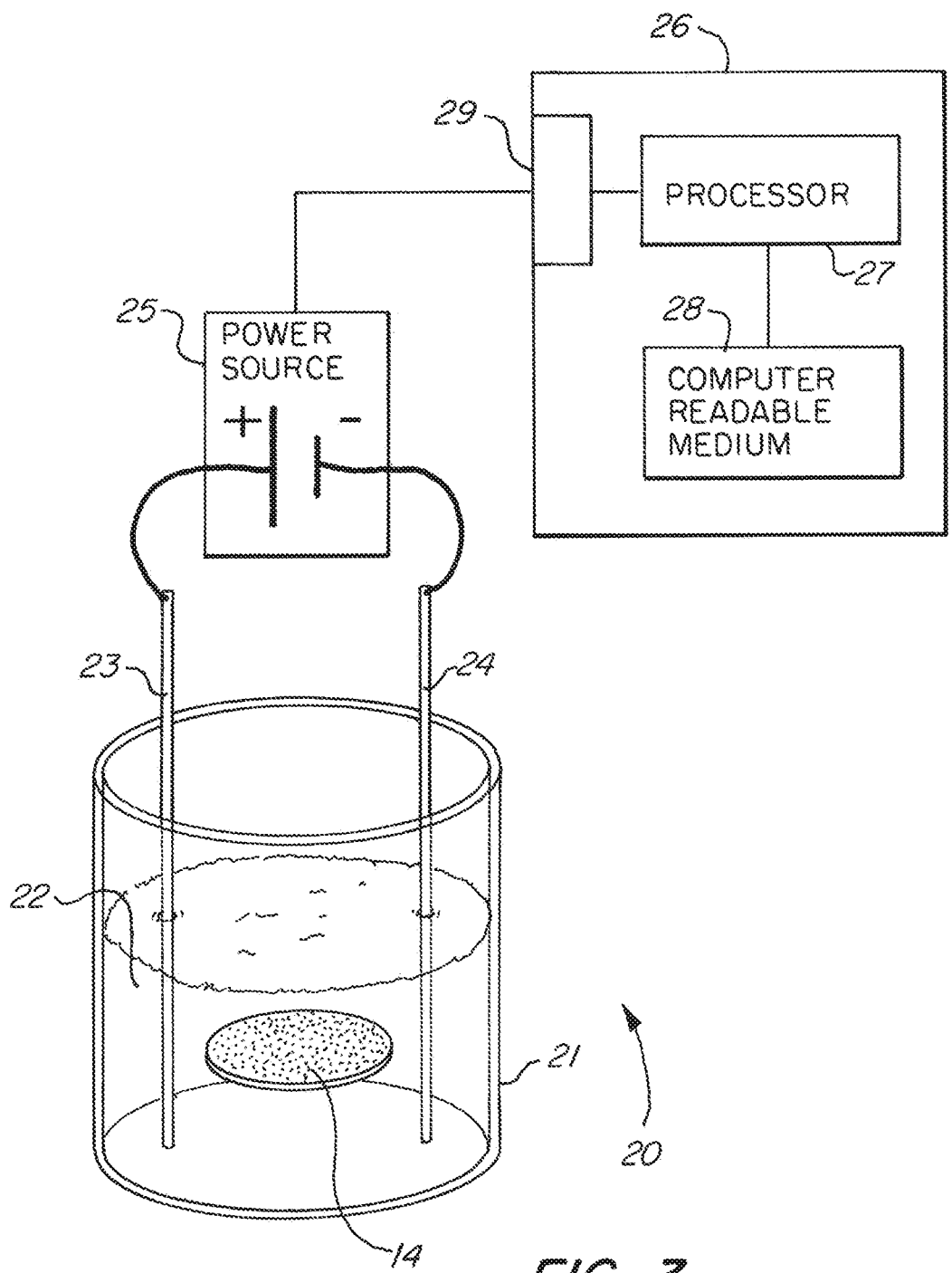
FIG. 3 is a diagram of a system according to a first example of the technology.

The system 20 has a process chamber 21, which is shown schematically in FIG. 3. The process chamber can be any vessel suitable for application of electric fields within; examples are a cuvette, a well of a multi-well device, a beaker and a tube. As an example, a cuvette adapted for electroporation (i.e. one with integrated electrodes) is used in some examples. The chamber 21 is adapted to hold a solution 22 appropriate for the blood sample that will not damage or alter it in such a way as to render it unsuitable for analysis. In general, solutions used in traditional DBS elution processes will work with the present technology. In this example, the solution used is a buffer solution. More specifically, the solution used is a phosphate buffered saline, containing 0.1% Tween 20 (polysorbate 80, a surfactant and emulsifier). Other examples also include a suitable amount of sodium azide, such as 0.08% sodium azide.

The chamber 21 is also adapted to receive two electrical conductors 23 and 24. These conductors are in the form of metal probes. In the example shown, the conductors 23 and 24 are connected to a power source 25. The power source 25 is adapted to create an electric potential difference between the conductors 23 and 24 so that an electric field exists between them. This is accomplished, in this example, by the power source 25 applying a voltage in the electrical circuit that contains the conductors 23, 24. In this example, the first conductor 23 is given a positive charge, while the second conductor 24 is given a negative charge when the voltage is applied. In other examples, different means for creating a difference in electrical potential between the conductors such that one of the conductors has a positive charge are used. For example, induction is used in some examples. In some examples, the electrical conductors 23, 24 are also coupled to motors for moving them into and out of the process chamber 21 as required.

As shown in FIG. 3, a portion 14 of a dried blood spot card is placed between the conductors 23 and 24 in the chamber 21. In some examples, the chamber 21 includes a specifically designed shelf or pedestal for the portion 14. In other examples, the chamber 21 includes a clip for securing the portion 14 against unwanted movement in the chamber 21. The system 20 also includes a controller 26 for controlling the power source 25 and any other functions of the system. In this example, the controller 26 includes a processor 27 and a computer readable medium 28. The controller 26 communicates with the power source via an interface or port 29.

In an example, the controller 26 controls the operation of the power source. In another example, the power source is manually operated. That is, in this example, it permits the system to apply a voltage at various amounts and for various lengths of time, as described in additional detail below. The computer readable medium 28 is in the form of a hard drive, such as a traditional or solid-state hard drive. The computer-readable medium 28 contains, in some examples, software that automatically controls the operation of the system. In some examples, the software will control the power source 25 to switch on at a selected voltage level for a selected time in response to user instructions. The software will also control the movement of the conductors 23, 24 into and out of the chamber 21 in examples in which motors are employed to move the conductors.

Figure 4:
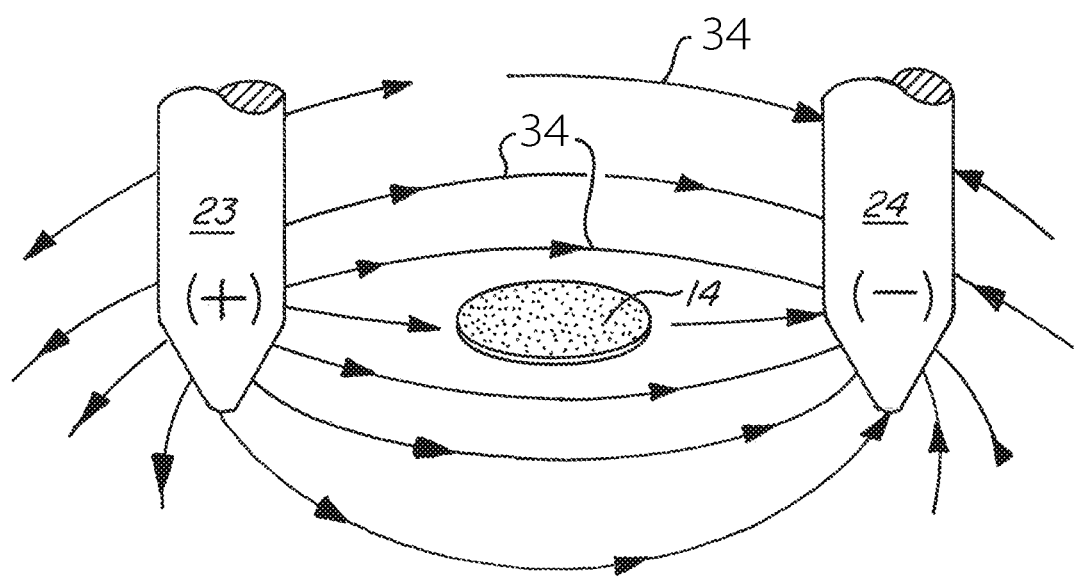
FIG. 4 is an illustration of the operation of the system of FIG. 3.

FIG. 4 shows a close-up schematic view of the tips of the conductors 23 and 24 and the portion 14 when the system 20 is in operation. Electrical field lines 34 show the electric field created when the power source creates a difference in electrical potential energy between the conductors 23 and 24. The arrows associated with the electric field lines 34 show the direction a positively charged particle would move, since the first conductor 23 has a positive overall charge as a result of the difference in electrical potential energy between the conductors.

Figure 5:
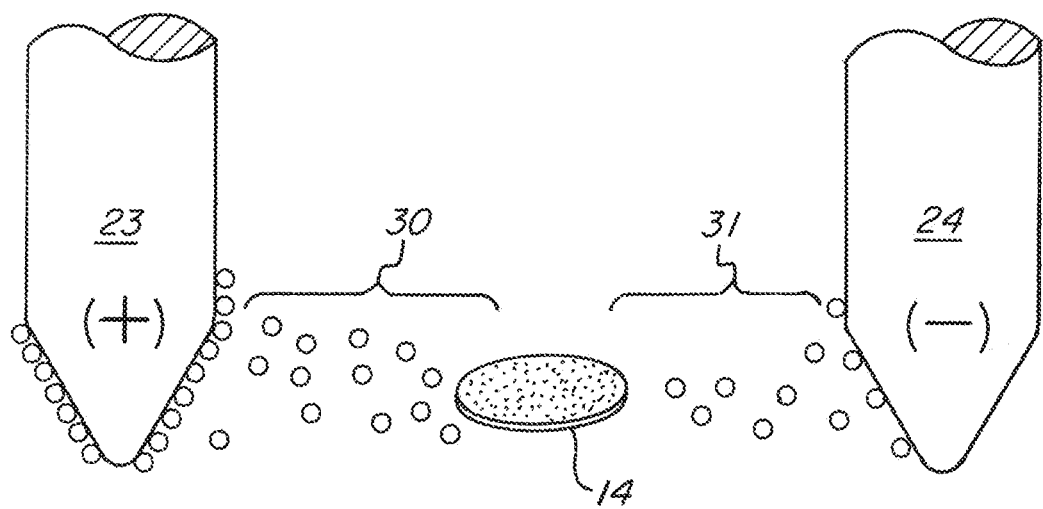
FIG. 5 is a second illustration of the operation of the system of FIG. 3.

FIG. 5 schematically shows the migration of bioanalytes from the portion 14 to the conductors 23, 24. Because conductor 23 has a positive charge, bioanalytes 30 of having a negative charge will move from the portion 14 of the sample storage medium to the conductor 23. These bioanalytes will include nucleic acid molecules such as DNA and RNA, as these molecules generally have a negative charge. The particles 31 are shown migrating to the negatively charged conductor 24 because such bioanalytes have a positive charge.

As a result of the difference in electric potential energy created between the conductors, bioanalytes that have an electric charge will be pulled from the portion 14 and attracted to one or the other of the conductors 23, 24. As shown in FIG. 5, once the potential difference has been applied for a selected duration, the conductor 23 will have an amount of negatively charged bioanalytes, which will include, in this example, nucleic acids, on its surface. At this point, the potential difference can be reduced to stop the particle migration. In some examples, the potential difference is maintained at a reduced level sufficient to retain the particles on the conductor. The conductor 23 is then removed from the process chamber 21 and is then inserted into a material collection chamber so that the particles can be collected and then further processed for analysis.

Figure 6:
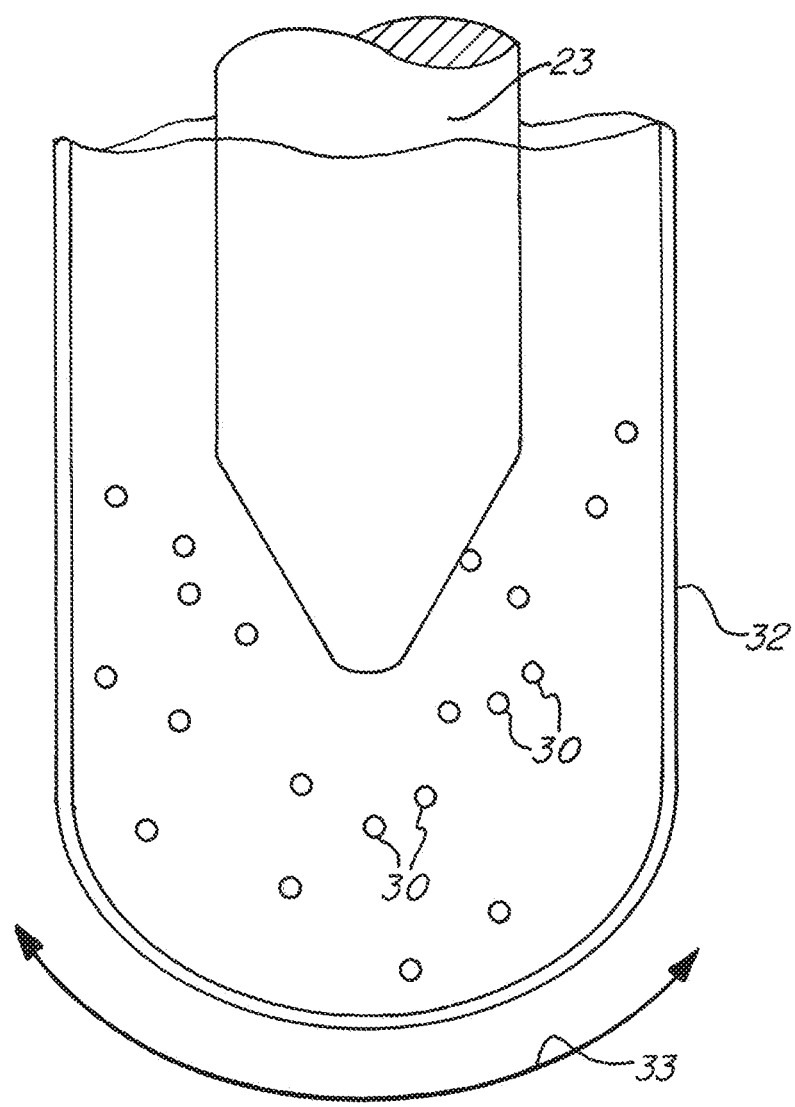
FIG. 6 is a close-up illustration of a portion of the system of FIG. 3 positioned within a material collection chamber.

FIG. 6 shows a schematic of a material collection chamber 32, with the conductor 23 inserted therein. The material collection chamber 32 can be any suitable vessel; examples are a cuvette, a well of a multi-well device, a beaker and a tube. In the example shown, the chamber 32 contains a buffer solution that will not damage or alter whatever biological sample is collected from the conductor 23. After the conductor 23 is inserted into the collection chamber 32, the difference in electric potential energy that causes the conductor 23 to have a positive charge is either eliminated or further reduced. This causes the negatively charged particles that were attracted to the conductor 23 to release from the conductor and disperse within the buffer solution in the chamber 32. In some examples, the chamber 32 is oscillated around the conductor 23 to impart movement to the solution that, in turn, exerts a force on the bioanalytes to assist in them being removed from the conductor 23. The oscillatory movement is indicated schematically by the arrow 33. Once the bioanalytes have been removed from the conductor 23, the solution can be transferred for further processing or for analysis.

Systems according to the present technology can take many different forms. In some examples, the system is a single purpose unit designed and programmed to extract various desired components from various substrates. For example, in some examples an electrophoretic cuvette acts as a type of cartridge that can be loaded into a purpose-built unit, which then automatically performs the necessary steps to separate bioanalytes from a substrate bearing a biological sample. In such a unit, the substrate is loaded into the unit which automatically extracts the appropriately sized portion. Then, once the cartridge is loaded, the unit automatically adds the appropriate type and amount of buffer solution as well as the portion of the substrate. In such an example, the cartridge contains integral electrical conductors that couple to the unit's control circuit to receive the necessary voltage. The unit can then apply the necessary voltages for the desired times to the conductors, then drain the buffer and leave the collected sample for dissolution in an appropriate buffer.

In other examples, the system has a wider range of applications for the use of the electric field to separate bioanalytes from a biological sample contained on a substrate. In some examples, the system includes features that permit adjustment of the distance between the conductors, adjustment of the location of the substrate or portion thereof, the use of different conductor shapes, and other features that expand the usefulness of the system.

In some examples, the system includes features that permit the isolation of specific types of bioanalytes. As used herein, the term "type of bioanalytes" means a group of molecules that share a common charge characteristic such that they are eluted together under a certain charge condition using the methods described herein. For example, nucleic acids (e.g. DNA, RNA) and proteins are known to have different electric charge profiles. By way of example, when the methods described herein are used to first collect DNA from a biological sample, the DNA is a first type of bioanalyte collected. If, subsequently, conditions were altered to allow collection of RNA, the RNA is a second type of bioanalyte collected. The electric field strength and duration can be tuned to select for elution of different types of bioanalytes. A "type of bioanalyte" can be a bulk collection of molecules, such as a pool of DNA eluted from a blood sample; and can also be selective for a particular fraction of bioanalytes. If desired, sequential elutions can be performed to collect different types of bioanalytes. As used herein, the term "bioanalyte" means molecules contained in a biological sample, such as nucleic acid molecules, e.g. RNA and DNA; proteins; lipids; and carbohydrates. These features include the ability to vary the amount of the difference in electric potential energy between the conductors. For example, if isolation of a first type of bioanalyte is desired and the first component is known to carry a certain amount of charge, the system can be set to apply a voltage that achieves the ideal difference in electric potential energy for attracting that first component to the exclusion of other components. The amount of the difference in electric potential energy is variable based on the selection of the user. The duration over which the difference of electric potential energy is applied is also variable based on the selection of the user. The duration can be varied in the system based on different migration times for different components of the sample from the storage medium to the conductor.

For example, if a sample is known to contain two types of bioanalytes that are of interest for analysis, and if the two types are known to carry different amounts of charge, a program can be used to isolate each type of bioanalyte from the substrate. A first amount of difference in electric potential energy can be applied using the system of FIG. 3 for a first period of time. The first amount of difference in electric potential energy and the first period of time are selected such that the first desired type of bioanalyte will migrate from the substrate to the conductor. This entails, for example, that the first amount of difference in electric potential energy is strong enough to move the first type of bioanalyte the required difference during the first period, but not strong enough to move the second type of bioanalyte that same distance during the first period. Once the first period is over, the difference in electric potential is reduced or eliminated so that the first type of bioanalyte can be collected. In some examples, collecting the first type of bioanalyte is the goal of the method, and unwanted bioanalytes remain behind on the substrate.

In other examples, the method involves obtaining a second type of bioanalyte, in which the conductors are returned to the process chamber and a second amount of difference in electric potential energy is applied for a second period of time. The second amount of difference in electric potential energy and/or the second period of time are selected so that the second type of bioanalyte will be attracted to the conductor. In some examples, these may be selected so as to exclude a third type of biological analyte, if such is undesirable once the second period has ended, the conductor is again removed from the process chamber so that the second type of bioanalyte can be removed from it. Additional types of bioanalytes can be collected by repeating this process.

More specifically, bioanalytes, e.g. DNA and RNA, are known to have different electric charge profiles in the presence of buffers at varying pH. This effect can be employed to selectively collect one type of bioanalytes by using one pH buffer in the process chamber containing the substrate, then changing to a second pH buffer in the process chamber to collect a different type of bioanalyte.

The performance of the system can be adjusted in other ways by various pre-processing steps and by adjusting, for example, the characteristics of the buffer used. For example, pre-processing steps to shake as well as incubate the substrate bearing the biological sample in a buffer have improved the sample yield. In other examples, multiple shaking and incubating pre-processing steps are utilized.

In still other examples, the pH of the buffer solution is adjusted to change the behavior of the bioanalytes in response to the applied electrical field. Some bioanalytes that have a negative charge in an approximately neutral pH solution will behave as if it has a positive charge when subjected to an electric field when the material is in solution that has a lower pH. In some examples of the present technology, the buffer solution used is varied according to the specific types of bioanalytes that the user desires to isolate, and a series of steps each employing buffers with different pH levels is used to isolate a series of different bioanalytes.

With reference again to FIG. 3, the computer readable medium 28 in some examples stores software for execution on the processor 27 that controls the electric power source to apply a voltage in a circuit connected to the first and second conductors so that the first conductor has a positive charge and the second conductor has a negative charge. The medium 28 also includes software that controls the source of electric power to reduce or eliminate the applied voltage so that bioanalytes separated from the portion of a substrate can be removed from the first electrical conductor. These functions are initiated by a user's interaction with one or more switches, a touch screen, or another suitable user interface.

In some examples, as described above, the software stored in the medium 28 includes programs for isolating one or more types of bioanalytes. For example, the software controls the source of electric power to apply a first amount of voltage for a first period of time in order to attract a first type of bioanalyte to the first electrical conductor. The software also controls the source of electric power to apply a second amount of voltage for a second period of time in order to attract a second type of bioanalyte to the first electrical conductor. The second amount of voltage is different than the first amount of voltage or the second period of time is different than the first amount of time, or both, in order to differentiate between types of bioanalytes hat have different amounts of electrical charge.

Similarly, software stored in the medium 28 controls the source of electric power to eliminate the applied voltage so that bioanalytes can be removed from the first electrical conductor after the first electrical conductor has been inserted into the material collection chamber.

Figure 7A:
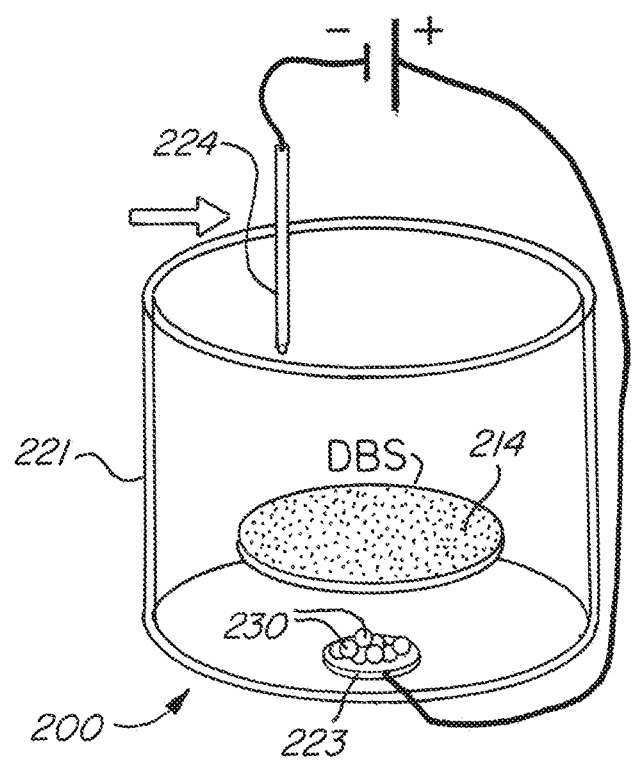
FIGS. 7a and 7b are diagrams of a system according to a second example of the technology.
Figure 7B:
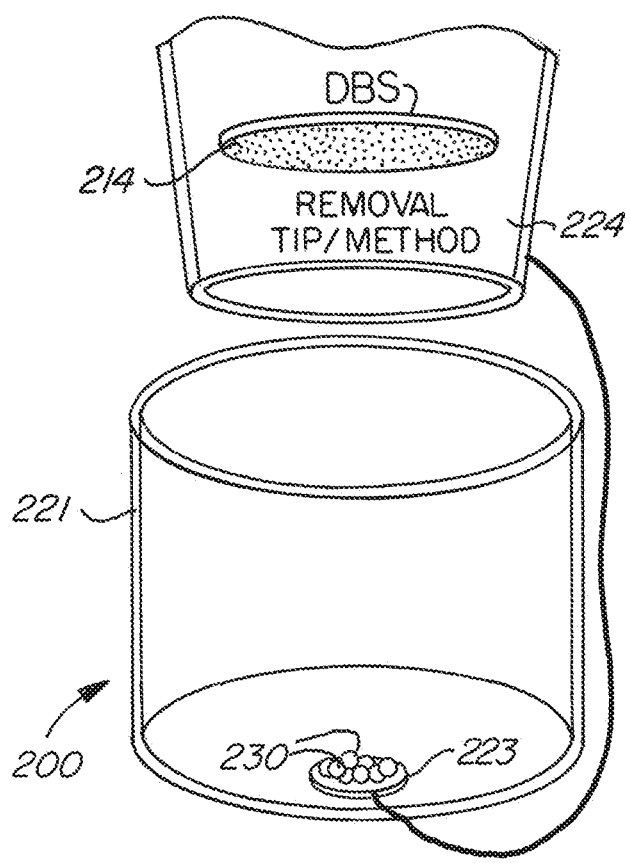

An alternative example of a system 200 for separating bioanalytes from a substrate bearing a biological sample is shown in FIGS. 7a and 7b. In this example, the system 200 has one electrical conductor 223 that is fixed to the process chamber 221. In this example, the portion 214 of the substrate is loaded above the conductor 223 and then a second conductor 221 is positioned above the portion 214. As shown schematically in FIG. 7a, negatively charged particles 230 are attracted to the conductor 223 once the voltage is applied to the system. In this example, the conductor 224 includes a reservoir tip, which is useful for removal of the portion 14 and any other bioanalytes in the process chamber at the desired time. This is shown schematically in FIG. 7b.

Figure 8:
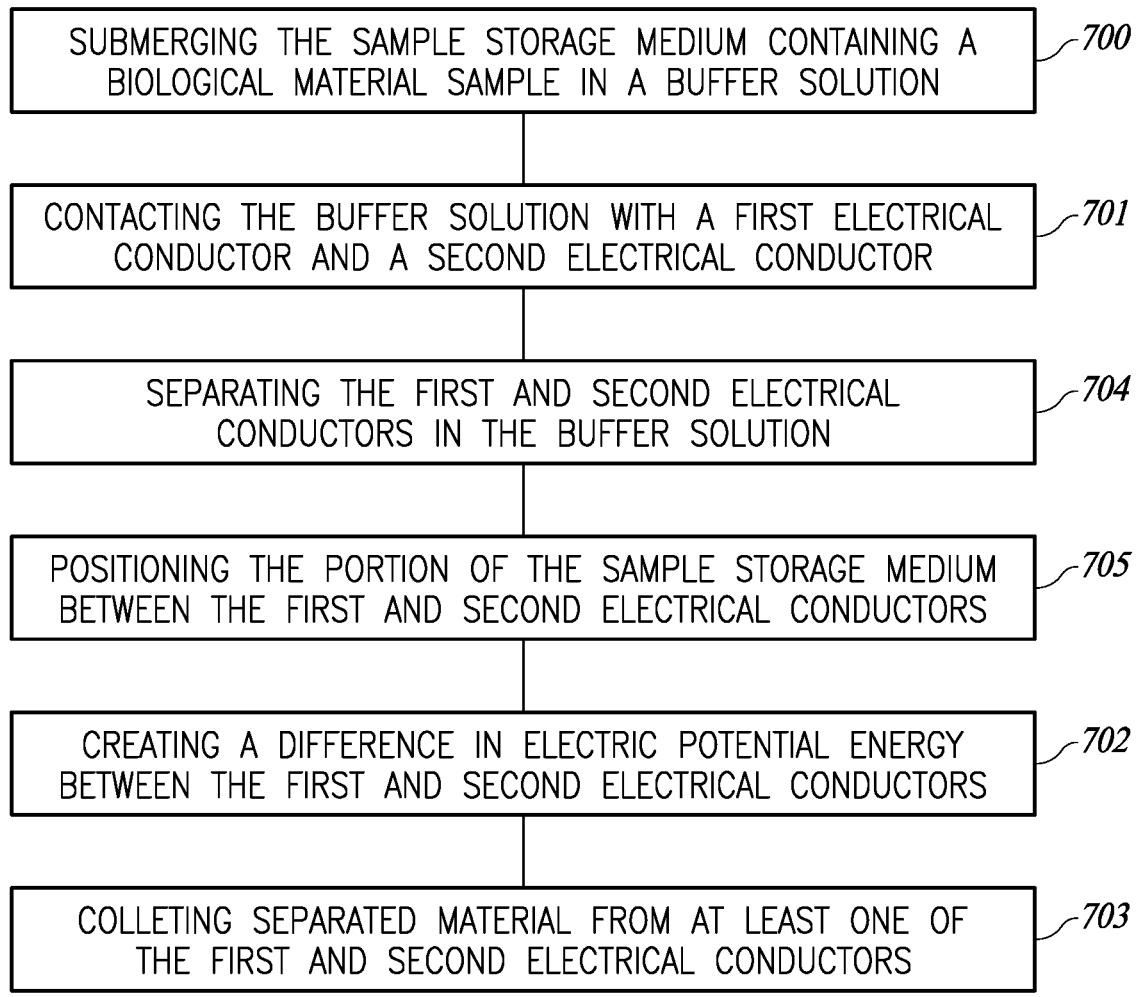
FIG. 8 is a flow diagram depicting a method according to an example of the present technology.

Examples similar to that of FIGS. 7a and 7b include those in which the process is undertaken involving a series of biological samples in, for example, a multiple well plate. In such examples, each well includes a fixed conductor. A second conductor, such as in the form of the conductor 224 in FIG. 7b, can be used to load the biological sample and buffer, then apply the electric field, and then remove the solution. This process can be done relatively rapidly over the series of wells. The present technology can also be embodied in various methods for separating bioanalytes from a substrate bearing a biological sample. FIGS. 8-12 show flow diagrams reflecting examples of these methods. As shown in FIG. 8, a method according to one example of the technology comprises first submerging the substrate containing the biological sample, such as a punch from a dried blood card, in a buffer solution at step 700. Then, at step 701, the buffer solution is contacted with a first electrical conductor and a second electrical conductor. At step 702, a difference in electric potential energy between the first and second electrical conductors is created. While the difference in electric potential energy exists, types of bioanalytes that have an electric charge will move in reaction to the force exerted on them by the electric field. Then, at step 703, the separated bioanalytes are removed from at least one of the first and second electrical conductors.

In some examples, the method also includes the step 704 of separating the first and second electrical conductors in the buffer solution and the step 705 of positioning the portion of the substrate between the first and second electrical conductors. Such additional steps may be necessary when using equipment or systems that do not have fixed or pre-selected positions for the conductors and sample placement. Steps 704 and 705 are manually performed by a technician or other individual preparing the sample in some examples, or, in other examples, they are automated using the system's electric motors and software settings and programs.

Figure 9:
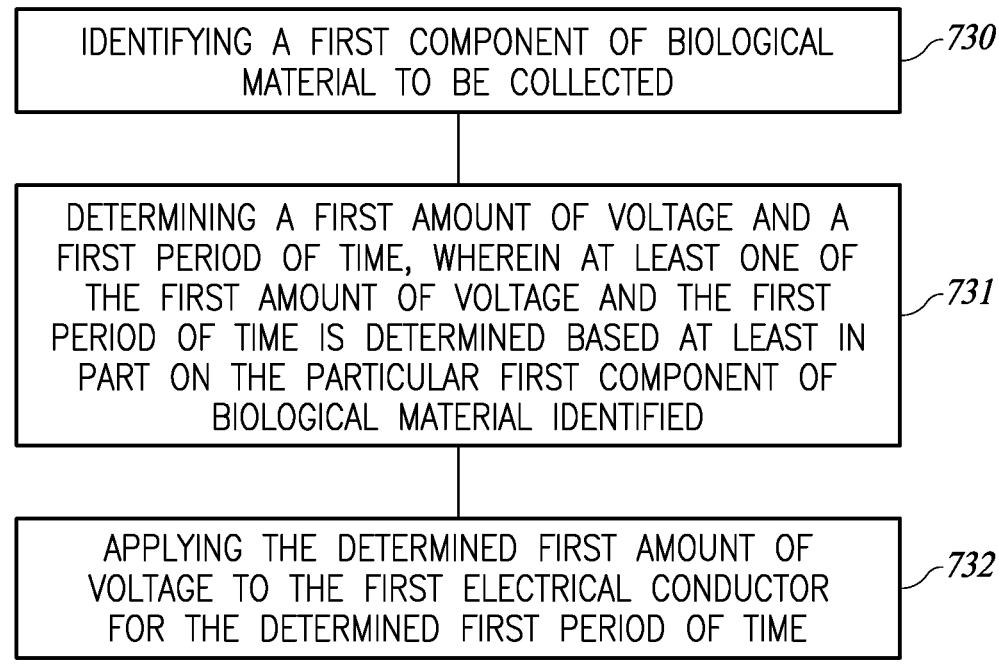
FIG. 9 depicts additional steps according to an example of the present technology.

In FIG. 9, additional details of step 702 are shown. In some examples, step 702 comprises applying a voltage to a circuit connected to the conductors, such that, the first electrical conductor has a positive electrical charge and the second electrical conductor has a negative electrical charge. In some examples, step 702 further comprises the steps of (730) identifying a first type of bioanalyte to be collected; (731) determining a first amount of voltage and a first period of time, where at least one of the first amount of voltage and the first period of time is determined based at least in part on the particular first type of bioanalyte identified; and (732) applying the determined first amount of voltage to the first electrical conductor for the determined first period of time. This process involves the user isolating a particular type of bioanalyte for collection and then applying the requisite voltage for the requisite time to attract the bioanalytes to a conductor. The same steps apply with respect to collecting a second type of bioanalyte, which requires either or both of a second amount of voltage applied and a second period of time over which the voltage is applied. Depending on the type of bioanalyte at issue, the second amount of voltage is different than the first amount of voltage or the second period of time is different than the first amount of time, or both of these conditions are true. In some examples, one or both of the voltage or the time of application is adjustable by the user according to his or her preference and the needs of the collection procedure.

In some examples, either one or both of the first amount of voltage or difference in electric potential energy or the first period of time is selected to attract deoxyribonucleic acid (DNA) to the first electrical conductor. Similarly, either one or both of the second voltage or amount of difference in electric potential energy or the second period of time is selected to attract ribonucleic acid (RNA) to the first electrical conductor. In this way, the user can employ the system to isolate RNA or DNA from the sample, or isolate both by performing the method serially.

Figure 10:
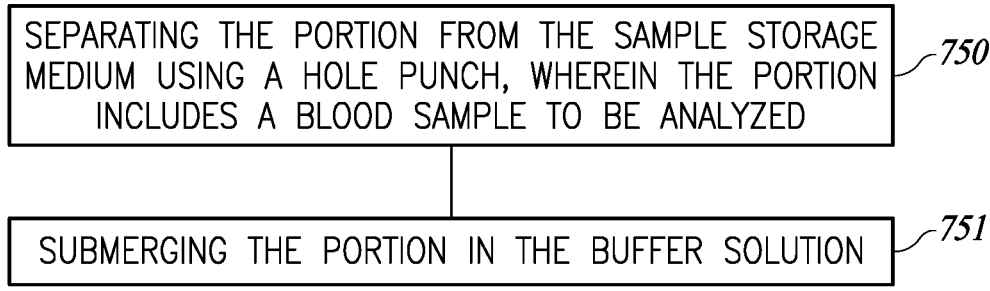
FIG. 10 depicts additional steps according to an example of the present technology.

FIG. 10 shows additional steps of the method according to some examples related to preparing a sample for processing. At step 750, a portion of the substrate is separated using a hole punch, where the portion includes a blood sample to be analyzed. The portion is then submerged in the buffer solution (step 751). In some examples, the substrate is a filter paper card, as in the traditional dried blood spot collection technique.

Figure 11:
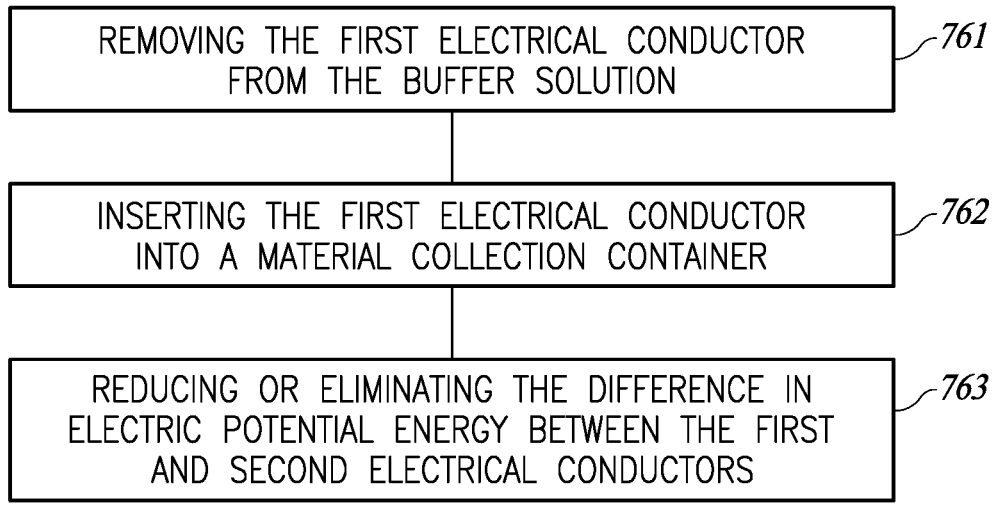
FIG. 11 depicts additional steps according to an example of the present technology.
Figure 12:
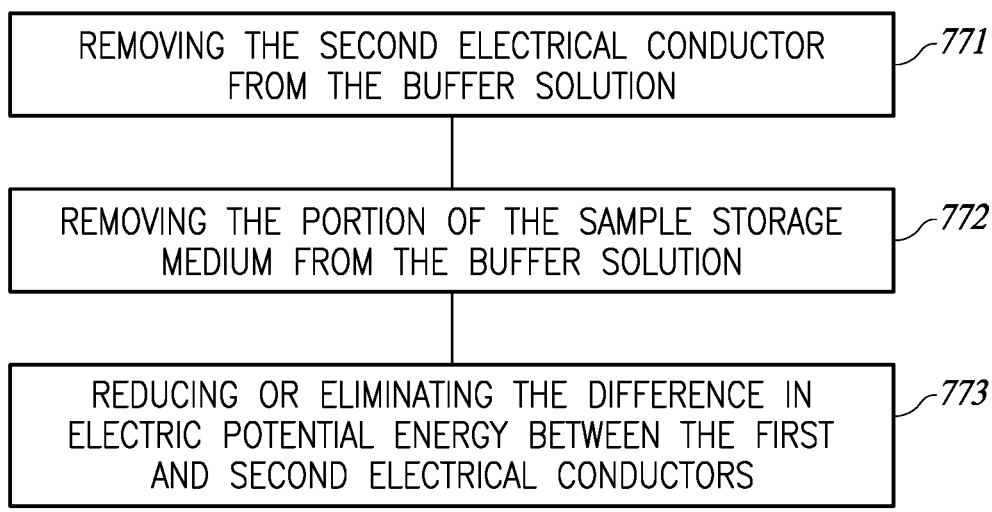
FIG. 12 depicts additional steps according to an example of the present technology.
Figure 13:
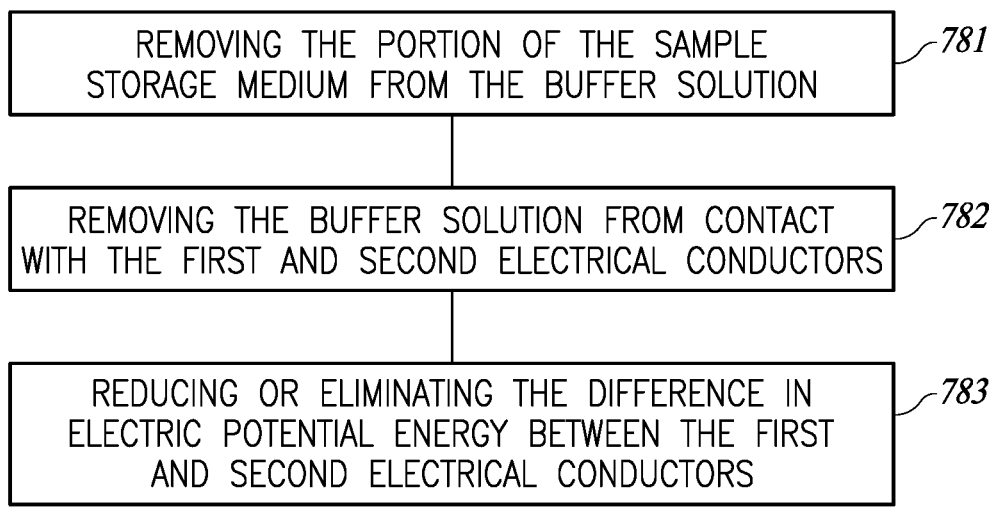
FIG. 13 depicts additional steps according to an example of the present technology.

FIGS. 11-13 show examples of additional steps related to collecting separated bioanalytes. In FIG. 11, step 761 includes removing the first electrical conductor from the buffer solution; step 762 includes inserting the first electrical conductor into a material collection container; and step 763 includes reducing or eliminating the difference in electric potential energy between the first and second electrical conductors. In FIG. 12, step 771 includes removing the second electrical conductor from the buffer solution; step 772 includes removing the portion of the substrate from the buffer solution; and step 773 includes reducing or eliminating the difference in electric potential energy between the first and second electrical conductors. In FIG. 13, step 781 includes removing the portion of the substrate from the buffer solution; step 782 includes removing the buffer solution from contact with the first and second electrical conductors; and step 783 reducing or eliminating the difference in electrical potential energy between the first and second electrical conductors.

In some examples, reducing the difference in electric potential energy is all that is required to permit the separated bioanalytes to separate from the electrical conductor. In other examples, the difference in electric potential energy is eliminated altogether in order to remove the separated bioanalytes.

EXAMPLES

In experiments, cord blood (PerkinElmer Waltham, MA) was prepared by centrifuging at 2500×g for 10 minutes at 4° C. The plasma was then discarded. Saline was added to the remaining blood mixtures and hematocrit was measured and adjusted to 48-53. 85 µL blood spots were then pipetted onto dried blood spot cards (PerkinElmer 226 Sample Collection Device, PerkinElmer, Waltham, MA). DBS cards were aged overnight and then punched into a 96 well plate using a Wallac DBS puncher (PerkinElmer, Waltham, MA).

To begin the extraction procedure, the 3.2 mm dried blood spot samples were placed into the wells of a 96-well PCR plate using clean forceps. DBS then underwent a series of wash steps with a detergent buffer. In short, 80 µL of wash buffer (1×PBS/0.1% Tween-20) was added to each well of the 96 well plate. The plate was then vortexed at 25° C. for 10 minutes at 700 rpm on a temperature controlled shaker (Thermoshake, Inheco, Martinsried, Germany). After the first incubation, the eluate was discarded and the wash step was repeated. A third wash step was performed by adding 80 µL of a lysis buffer (10 mM KOH/30 mM Tris buffer) to each well, and incubating for another 10 minutes at 25° C. and 700 rpm.

Figure 14:
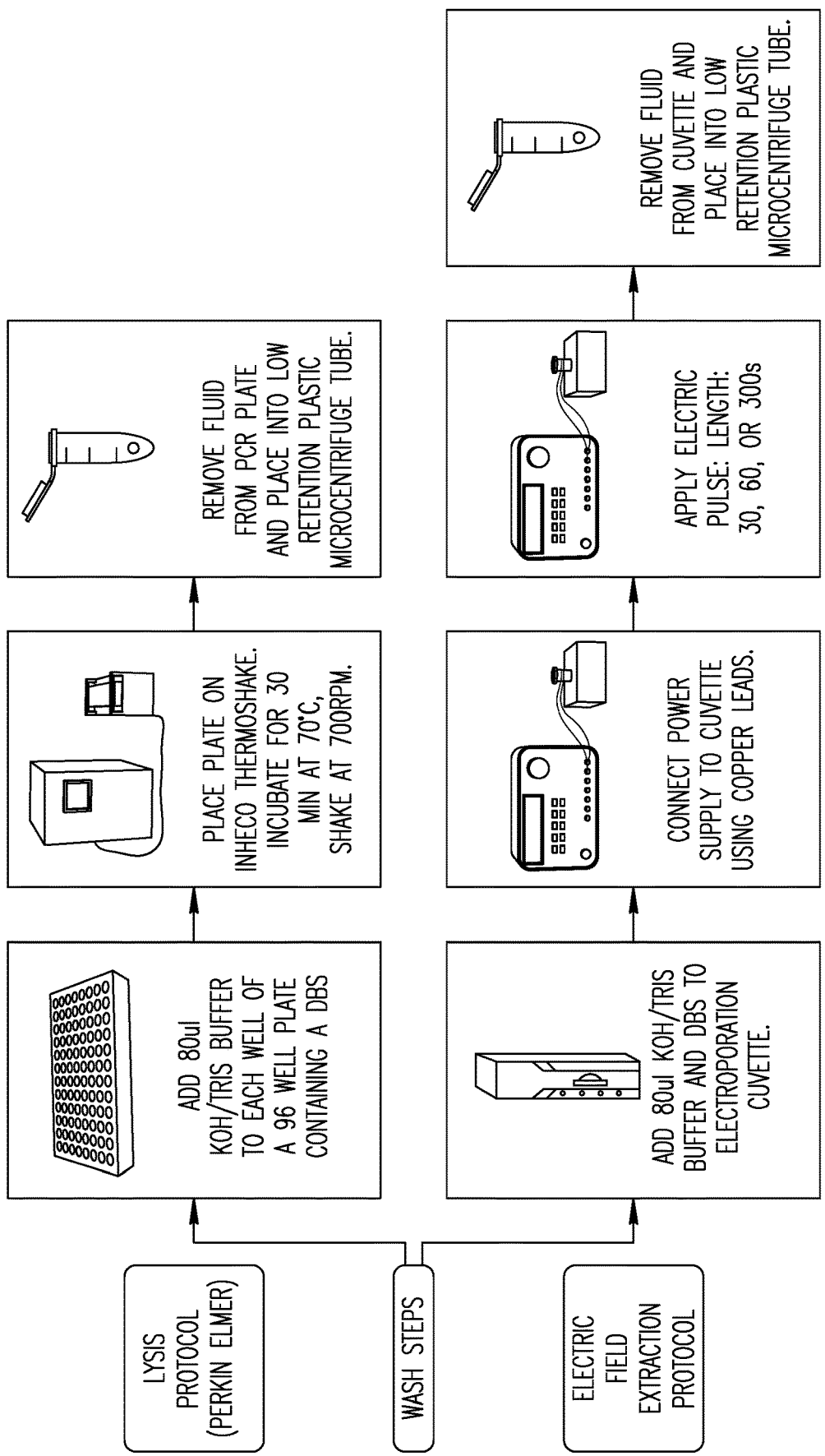
FIG. 14 depicts procedures for experiments according to an example of the present technology.

The same wash steps were used in both a proprietary Perkin Elmer lysis procedure and an electric field procedure, however, after this point the protocols differed significantly, as illustrated in FIG. 14. To perform the proprietary lysis procedure an additional 80 µL of lysis buffer (10 mM KOH/30 mM Tris buffer) was added to each well containing a DBS. The plate was then incubated at 70° C. and 700 rpm on a temperature controlled shaker (Thermoshake, Inheco, Martinsried, Germany) for 30 minutes. After this incubation the eluate from PCR plate was removed and analyzed immediately using qPCR.

DBS undergoing the electric field extraction procedure were removed from the PCR plate using clean forceps and placed in a Sigma-Aldrich© electroporation cuvette with a gap width of 0.1 cm. Cuvettes containing DBS and 80 µL of lysis buffer (10 mM KOH/30 mM Tris buffer) were then either subjected to a five-minute heating step or processed in the electric field immediately. Electric fields were then applied to the DBS-containing cuvette. At the end of each extraction, the supernatant was removed from the cuvette and analyzed immediately using qPCR.

To detect TREC extracted from DBS, real time quantitative PCR was performed. All experimental conditions were tested with at least three experimental samples and two technical replicates per sample were performed to assess experimental accuracy. Each PCR run of 20 µL contained 4 µL of sample, TaqMan 2×PCR Master Mix, and OneTaq® Hot Start DNA Polymerase (Applied Biosystems, Thermo Fisher Scientific, Waltham, MA). The probes used for this assay were labeled with FAM for TREC and HEX for the Ribonuclease P/MRP Subunit P30 gene (RPP30). RPP30 was used as a reference gene to assess PCR amplification and DNA extraction. Reactions were carried out on a Piko-Real Real Time PCR System (Thermo Fisher Scientific, Waltham, MA) using the following protocol: 5 minute denaturation at 94° C. followed by 44 cycles of 15 seconds at 94° C., 30 seconds at 60° C. and 15 seconds at 68° C. Fluorescence data from PCR amplification was analyzed using the Picoreal software and the R project statistical computing qPCR library. $C_t$ values were determined by two separate methodologies. First $C_t$ was calculated using a fixed threshold value of 170 for RPP30. Further analysis of the raw fluorescence data included a sigmoidal fitting of the amplification curves with a five parameter log-logistic curve in order to identify outliers and obtain both the second derivative maximum, cpD2, and Cy0 numbers. Copy number was obtained from the raw $C_t$ values. TREC and RPP30 copy numbers were calculated by a tenfold dilution series of $10^5$ copies of linearized plasmid (PerkinElmer, Waltham, MA, USA). A standard curve was created for both plasmids by plotting the $C_t$ numbers against the number of copies of the plasmid. Extraction efficiency was assessed using percent yield, which was calculated from literature values. For an extraction of 100% efficiency, a 3-mm dried blood spot was considered to contain 3.47 ng/µL of genomic DNA.

Double stranded DNA was quantified with a Quant-iT™ PicoGreen® dsDNA kit (Invitrogen, Eugene, OR, USA). Each experimental condition was tested using three experimental samples (DBS), and duplicate aliquots were evaluated for each experimental sample using PicoGreen analysis. PicoGreen reagent was prepared as a 1:200 dilution with TE buffer (pH 7.5). Experimental samples were diluted in a 1:10 dilution in TE buffer to reduce inhibitors in the sample. 20 µL of each sample was added to 20 µL of the PicoGreen reagent working solution in a black 384-OptiPlate (PerkinElmer, Waltham, MA, USA) and was read using a fluorescence plate reader (EnVision 2105 multimode plate reader (PerkinElmer, Waltham, MA, USA)) at an excitation wavelength of 485 nm and an emission wavelength of 535. Lambda DNA (supplied by the manufacturer) at a concentration of 100 μg/mL was used to construct a standard curve. Blank values and background were subtracted from experimental data.

Statistical analysis of electric field extraction of DNA from dried blood spots was performed using multi-factor ANOVA. The Tukey HSD test was used to evaluate the statistical significance of interactions between each factor's levels. The three factor ANOVA to evaluate the experimental optimization had the following factors and levels: KOH concentration (5 mM, 10 mM and 15 mM), applied voltage (10V, 25V, 50V) and time of pulse (30 s, 60 s, 300 s). A p-value of 0.05 was considered to be statistically significant. Statistical analysis was performed using an XLSTAT statistical software package (Addinsoft, New York, NY).

Figure 15:
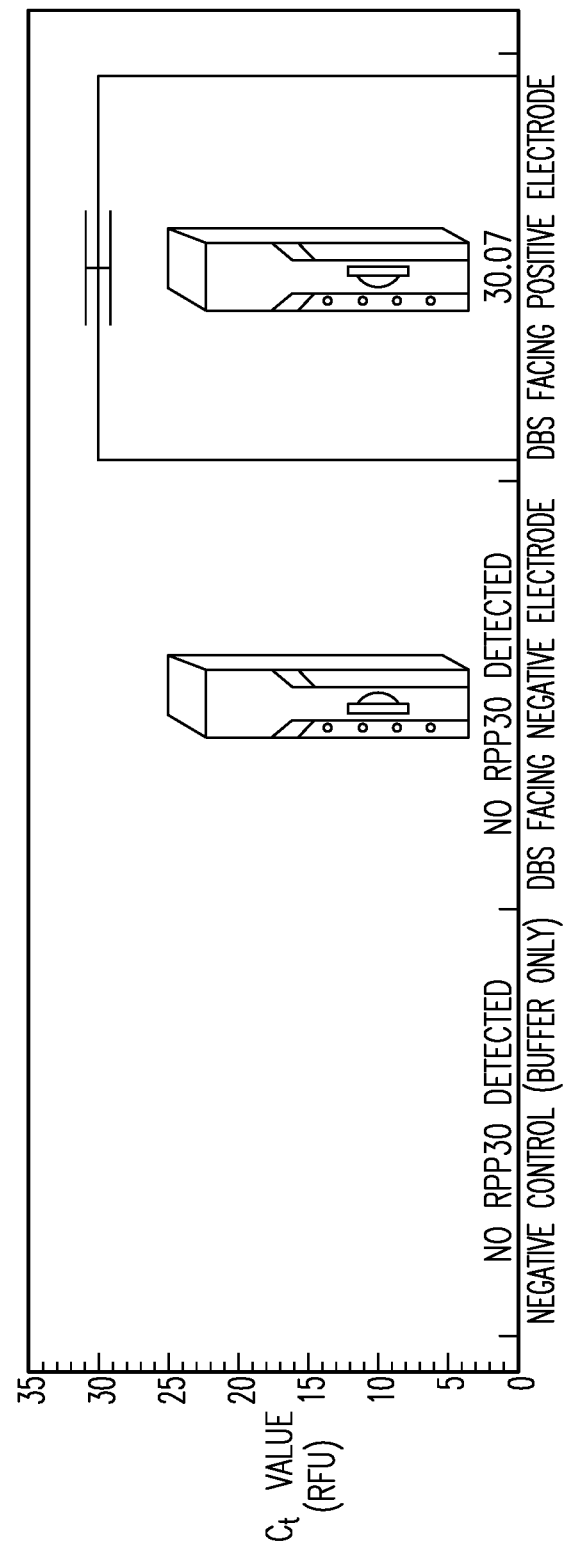
FIG. 15 depicts results of the experiments according to an example of the present technology.

To evaluate the feasibility of extraction of genomic DNA from DBS using an electric field cuvette device, a proof of concept experiment was performed, with the results illustrated in FIG. 15. In this experiment DBS were oriented in one of two directions, either with side of the filter paper spotted with cord blood facing the negative electrode or with the side of the filter paper spotted with cord blood oriented toward the positive electrode. The results of this experiment showed that no RPP30 or TREC was detected when the blood spotted on the paper was facing the negative electrode. A control where a DBS and buffer was added to the cuvette also showed no amplification of RPP30. This suggests that the electric field alone was responsible for the DNA extracted from the surface.

Figure 16A:
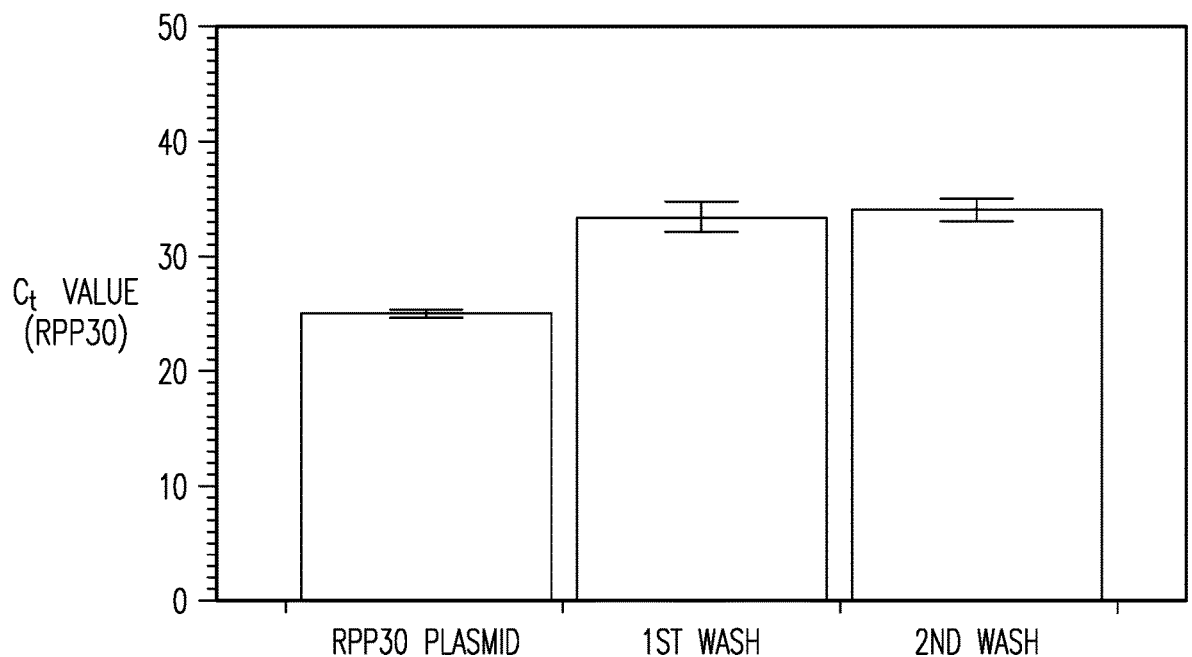
FIGS. 16A and 16B depict results of the experiments according to an example of the present technology.
Figure 16B:
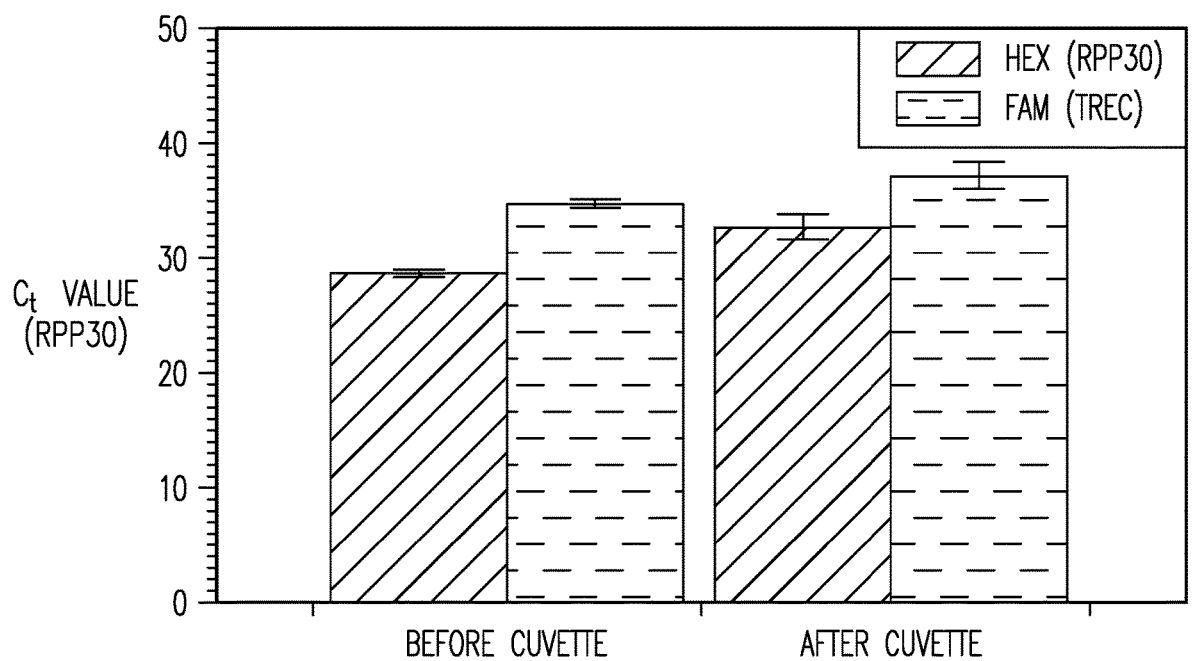

Accurate measurement of the extraction efficiency from the electric field procedure required a thorough characterization of known limitations on yield found in the system such as adhesion to the plastic of the cuvette. Quantification of DNA has been shown to be strongly affected by adhesion to standard plastics, reducing DNA retrieval by up to 50% by comparison to low retention plastics. Three investigations with retrieval of a solution of $10^3$ copies/μl of linearized RPP30 plasmid from the surface of the polystyrene electroporation cuvette showed an average reduction of 55% in the copy number of plasmid recovered from the tube (results are illustrated in FIG. 16A). A wash of the surface with Tris buffer solution retrieved an average of 70% of the copy number of the original plasmid solution indicating there was still plasmid adhered to the plastic of the tube. To further evaluate adhesion to the plastic surface, eluate from the lysis procedure was added to an electroporation cuvette and allowed to sit for a period of 5 minutes. The eluate was then removed from the cuvette and three biological replicates were tested using both qPCR and a Picogreen assay for dsDNA (results are illustrated in FIG. 16B). Substantial increases (p=0.012) in the average $C_t$ value of the lysis protocol occurred after exposure to the plastic cuvette.

Figure 17A:
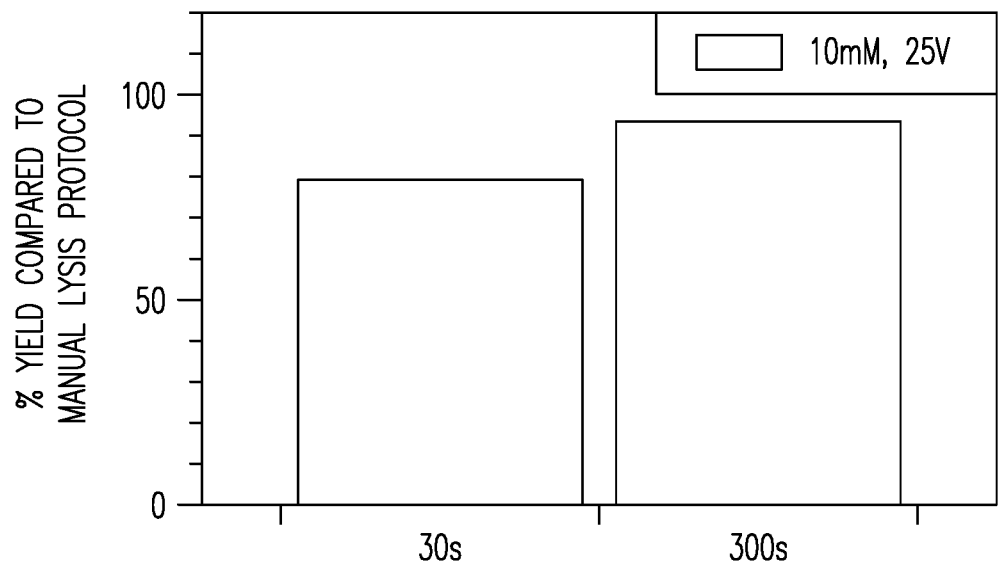
FIGS. 17A, 17B, and 17C depict results of the experiments according to an example of the present technology.

The optimization of the system and protocol for DNA recovery was continued with an in depth look at three parameters of the electric field procedure: time of the pulse applied across the cuvette plates, strength of the voltage applied across the cuvette plates, and the concentration of KOH in the lysis buffer solution. The housekeeping gene, RPP30, was used to measure the variation in genomic DNA extracted from the DBS and as a preliminary method of assessing its quality. Three biological replicates for each experimental condition were used for real-time PCR analysis and two technical replicates were analyzed for each biological replicate to assess experimental accuracy. The results of these investigations can be seen in FIGS. 17A-17C. Evaluations of pulse time at 10 mM and 25V showed decreases in $C_t$ with increasing pulse time. Evaluation of the molar concentration of KOH in the buffer showed that KOH in excess of 10 mM lead to slight decreases in the yield of DNA from the electric extraction. Optimal recovery was seen at 10 mM, 25V and 300 s, recovering 93% of DNA captured by the lysis procedure.

Figure 17B:
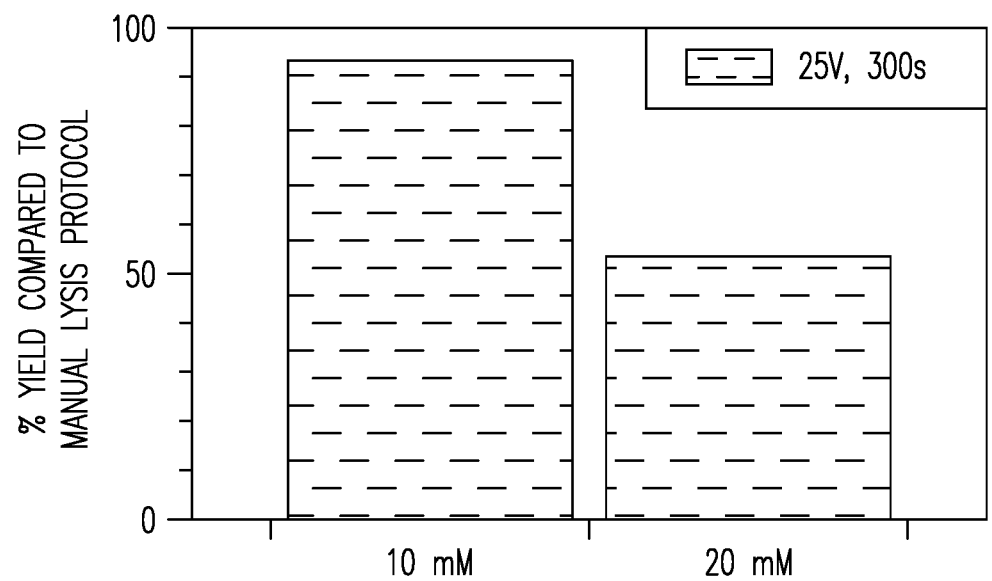
Figures 17C, 18:
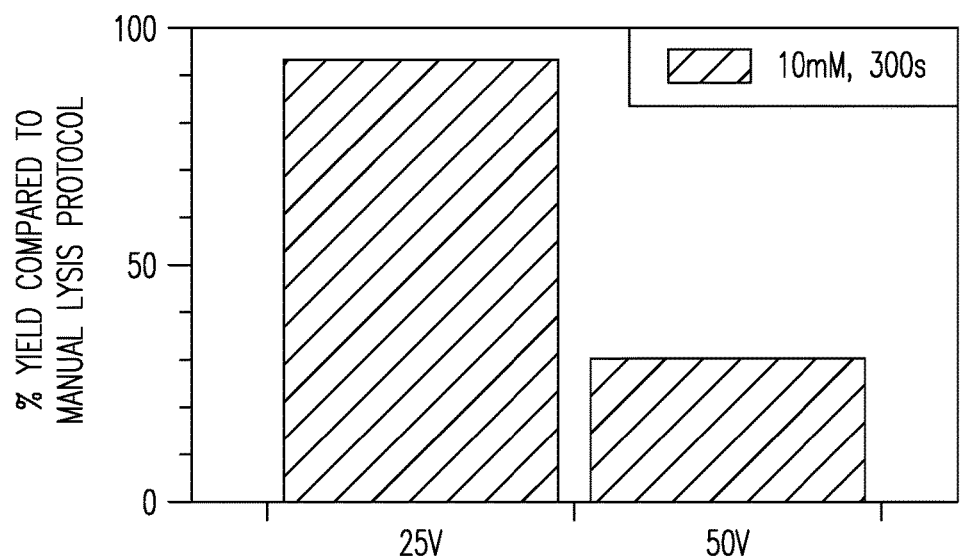
FIG. 18 depicts results of the experiments according to an example of the present technology.

Additionally, this procedure reduced the time of the proprietary lysis procedure by a total of 25 minutes. Higher voltages and molar concentration of KOH in the buffer lead to significant decreases in the recovery of DNA from DBS (p=0.050, two way ANOVA) (FIG. 17B). This suggests that recovery of DNA at 10 mM and 25V may be unaffected by harmful changes in the environment of the cuvette such as bubble formation, heating and dramatic pH changes caused by hydrolysis. These effects have been linked to pulse time in electroporation. Further quantification of dsDNA was performed using a Picogreen assay and can be seen in FIG. 18. Three biological replicates per experimental condition were analyzed using the Picogreen assay. Two technical replicates were performed for each biological replicate. The Picogreen assay confirmed that the presence of dsDNA within the 10 mM, 25V, 300 s electric sample was significantly different than samples exposed to buffer alone (p=0.050).

Figure 19:
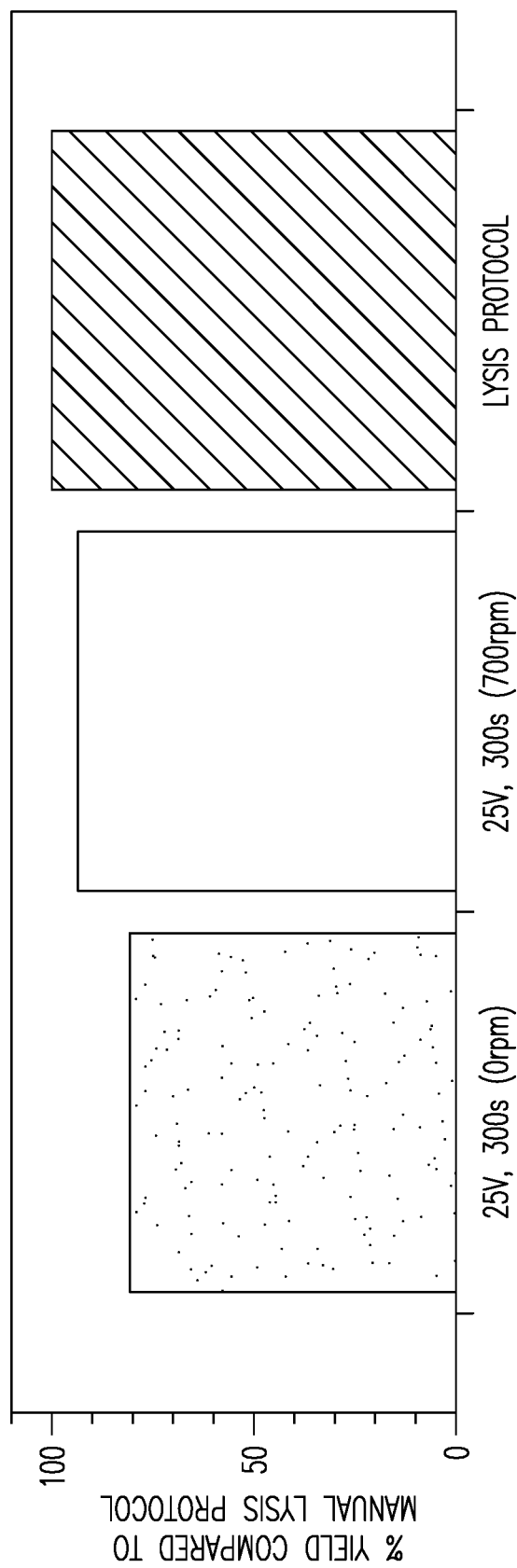
FIG. 19 depicts results of the experiments according to an example of the present technology.

Scale up to automation is another important part of the creation of a viable methodology for DNA extraction from dried blood spots. The high throughput analysis of an automated DNA extraction would be especially beneficial for large scale genetic testing such as newborn or neonatal screening for primary immunodeficiencies. Automation increases efficiency and accuracy, standardizes sample handling, and limits human contact with potentially infected materials making it a highly effective strategy to process clinical samples like DBS. To create a fully automated system, certain requirements of the proprietary lysis protocol needed to be changed. Most significantly, vortexing needed to be removed from this protocol. Thus, an optimized electric procedure without vortexing in the wash steps was developed. Samples were analyzed using real-time PCR with three biological replicates for each experimental condition and two technical replicates to assess experimental accuracy. As seen in FIG. 19, the yield from this improved procedure for automation was 81% of that of the proprietary lysis procedure. The removal of vortexing from the wash steps reduced the time of the wash steps by half, not only simplifying the procedure but saving an additional 15 minutes over the original electric procedure. The total time of the optimized electric procedure without vortexing was 20 minutes.

To design a procedure without vortexing that would preferentially yield episomal DNA from the DBS, optimizations to the previous protocol were necessary. High temperature extraction methodologies are commonly used for plasmid isolation and preparation within the literature and are particularly suited to episomal DNA recovery. Initial testing on vortexed samples showed the addition of a 5-minute heating extraction step at 70° C. caused a significant decrease in the $C_t$ of RPP30 (p=0.032, two-way ANOVA). Thus, to increase episomal DNA recovery, a 5-minute heat-based extraction was added to the electric protocol. The temperature, location, and duration of the heat-based extraction was assessed using qPCR.

Figure 20A:
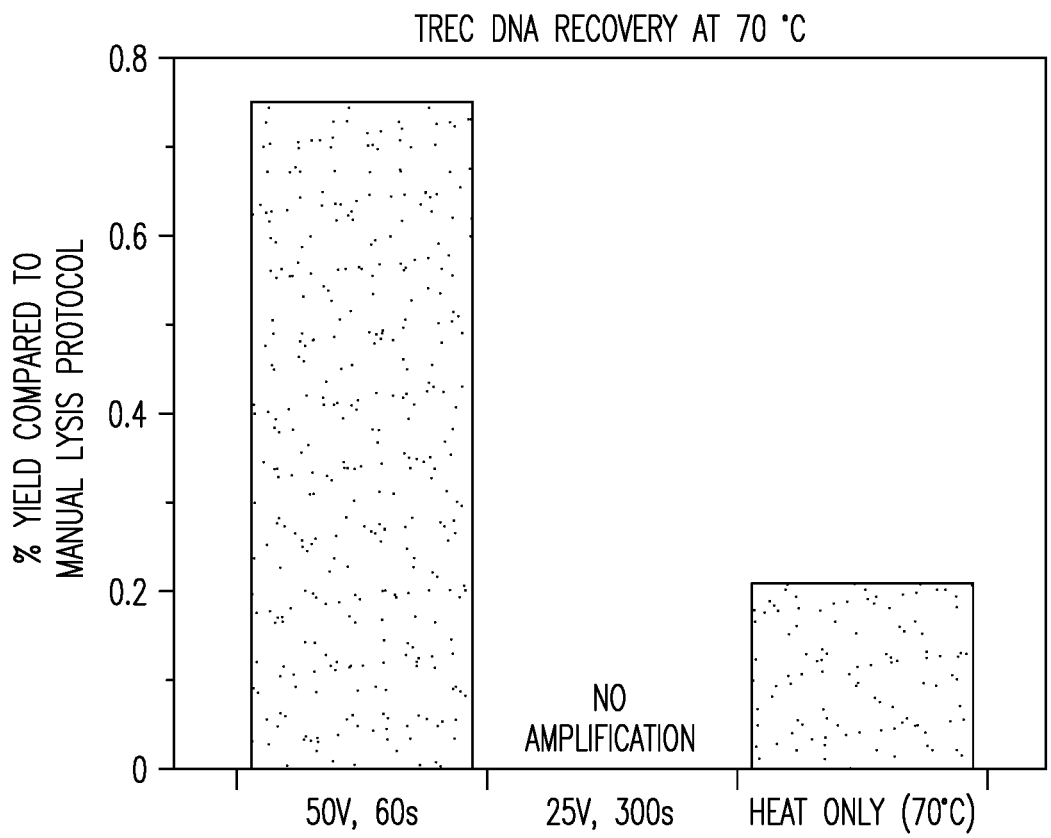
FIGS. 20A, 20B, and 20C depict results of the experiments according to an example of the present technology.
Figure 20B:
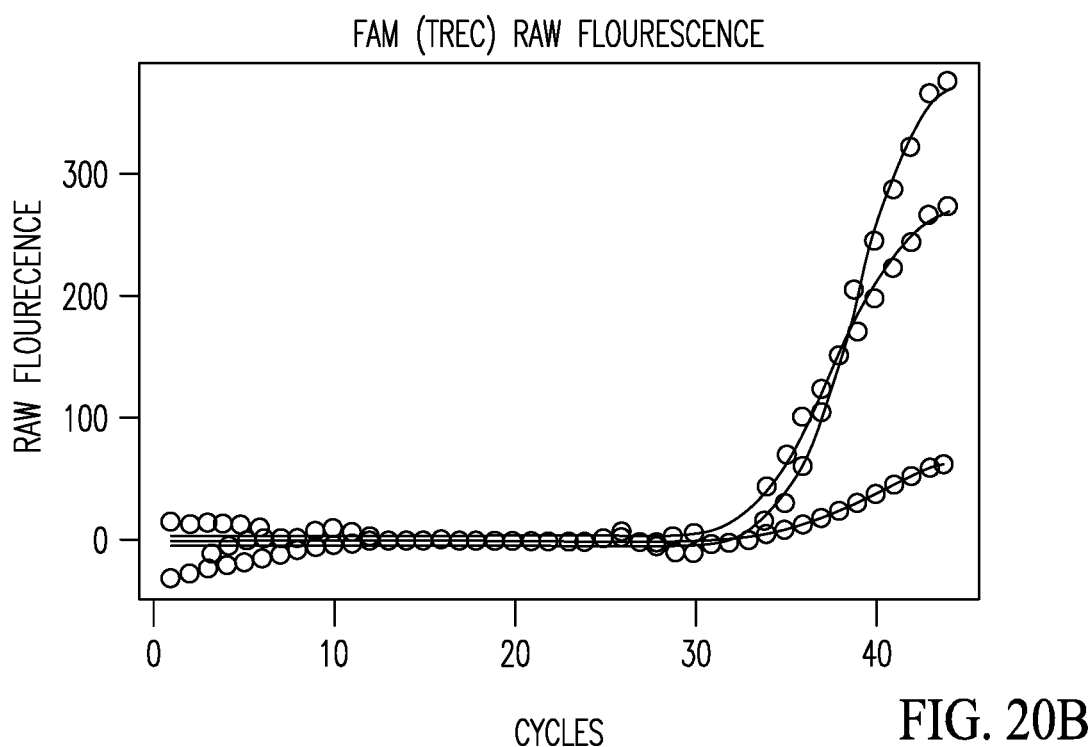
Figure 20C:
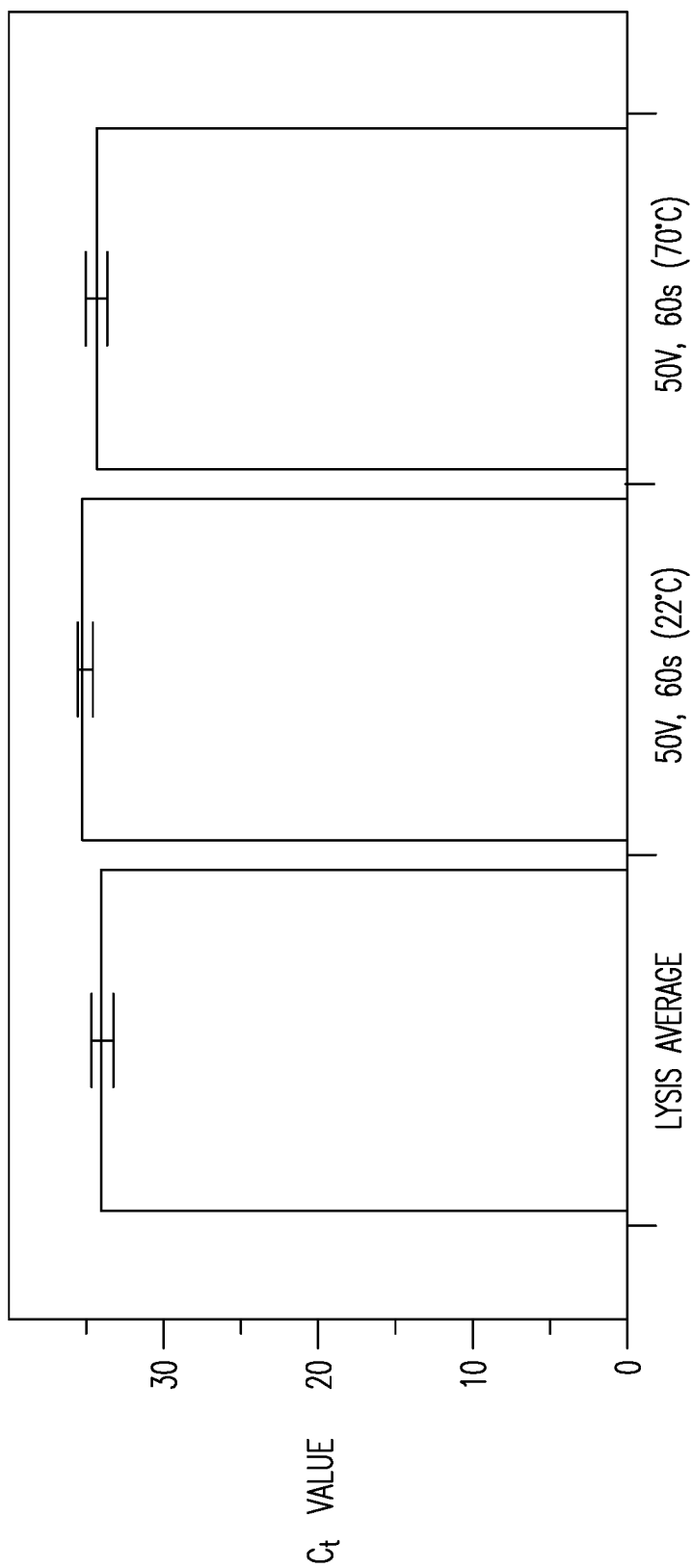

FIG. 20A shows the average yields of three biological replicates for two conditions of the optimized 70° C. heating procedure for non-vortexed samples. No amplification was seen from the 25V samples for TREC episomal DNA. A substantial decrease in the $C_t$ value of the non-vortex samples occurred at 50V, 60 s, as illustrated in FIG. 20B. These results were statistically different than that of the control, heating alone (p=0.006). As seen in FIG. 20A, samples processed at 50V, 60 s yielded 75% of the total yield of the manual lysis procedure. FIG. 20C compares the $C_t$ values the 50V, 60 s samples at 70° C. and samples without the added heating step (22° C. (room temperature)). By combining the two methodologies, yields were increased above the yield of either method alone.

To predict, assess, and compare the experimental parameters of the DBS extraction system, a mathematical analysis of the properties of the cuvette system was performed. Simulation of the electric field within the extraction device was carried out using the AC/DC module of COMSOL Multiphysics (v5.3, COMSOL Group, Burlington MA). Two distinct 2D model geometries representing the experimental conditions tested within the model system were designed. Each model consisted of three parts, two parallel stainless steel electrodes, an electrolyte buffer region, and a model of the dried blood spot. To perform the finite analysis, each area was meshed with a free triangular mesh. The minimum element size of this mesh was 0.001 cm and a grid independence study confirmed that the calculated solution was independent of the mesh size.

Boundary conditions for the model were prescribed as follows: potential at the edge of the first stainless steel electrode was set as the voltage applied during the experiment (25V or 50V). The remaining electrode was then defined as a ground. The DBS was modeled as a 3.2 mm×0.33 mm rectangular region located in the center of the model. The conductivity of this region was approximated as 0.7 S/m the conductivity of blood. This approximation neglects the contribution of the filter paper to the conductivity of the DBS. Recent studies suggest that the filter paper makes little difference in the value of the conductivity of a dried blood spot and that greatest contribution to conductivity of a DBS comes from the ion concentrations in the blood itself. The relative permittivity of the DBS was set as 5260. The conductivity of stainless steel was set at $1.45 \times 10^6$ S/m and the conductivity of the KOH/Tris buffer was determined to be 0.133 S/m using a conductivity meter (Horiba Laquatwin B-771 Horiba Ltd.).

An LCR meter was used to calculate the dielectric constant of the KOH/Tris buffer from the measured capacitance from between the plates of the electroporation cuvette. Values obtained (6.92) were in good agreement with literature values for KOH buffers. Diffusion coefficients for OH$^-$ and K$^+$ ions were taken from the literature and were as follows: $5.23 \times 10^{-9}$ and $1.9 \times 10^{-9}$. Simulations were run for voltages of 50V and 25V. The simulation results showed a roughly uniform electric gradient generated across the plates of the cuvette with an electric field strength of 500 V/cm for the 50V experiment and 250 V/cm for the 25V experiment. This shows that the cuvette is suitable for DNA removal from the DBS and for DNA free fluid electrophoresis. Importantly, other than the strength of the electric gradient generated across the longitudinal gap, there were no significant differences between the model systems. This suggests that forces from the electric field are the main factor in removal of DNA from the DBS.

These experiments facilitated in-depth analysis and optimization of electric field extraction to remove DNA from DBS. Currently, methodologies available for DNA extraction from DBS are laborious and time consuming, and consist of many steps that are less than ideal for automation. The procedures described herein not only reduce the time of the proprietary procedures by more than 30 minutes, but also negate the need for costly treatment and wash steps, while retaining the recovery of episomal DNA from the DBS.

The procedures described herein show the feasibility of DNA extraction by electric field. Additionally, the procedures described herein were optimized for TREC episomal DNA, and achieved genomic and episomal DNA recoveries in the 25V, 300 s and 50V, 60 s procedures that were not significantly different than the recoveries of the proprietary lysis procedure. The 25-minute extraction time from the optimized electric field DBS lysis procedure is the lowest procedural time for episomal DNA extraction currently known within the literature.

The procedures described herein allow for the removal of time consuming wash steps which rely heavily on vortexing to improve DNA yield. Not only were these new procedures able to remove these time and energy-consuming steps, but to retain more than 80% of the yield of RPP30 and 75% of the yield of TREC of the proprietary lysis procedure. Early results also suggest that TREC DNA can be recovered from DBS exposed to a dual electric field extraction (25V, 300 s and then 50V, 60 s ($C_t$ 34.87)). As seen in investigations of the orientation of the DBS, the cellulose fiber matrix of the dried blood spot has a direct effect on the migration of DNA out of the filter paper. Long DNA molecules, such as TREC episomal DNA, have been shown in the literature to remain trapped within the network of the filter paper even after cell lysis and wash steps. This effect is thought to be caused by DNA entanglement with fiber matrix of the paper and is dependent on the pore size of the paper.

The purity of the DNA retained on the fiber matrix of the paper is also influenced by the porosity of the fiber matrix. If the pores in the paper are too large, DNA is released from the paper. If they are too small, inhibitors can be retained. Using the matrix of the filter paper to hold the episomal DNA may provide a method to remove inhibitors and pre-purify DBS samples. This DNA could then be removed from the DBS by using higher voltages. Computational analysis of the electroporation system showed uniform electric gradients generated across the plates of the electroporation cuvette model and suggests that the electric field is the main factor in the removal of the DNA from the DBS.

Adhesion to standard plastics has been shown to strongly affect the quantification of DNA, and our study shows significant increases in the $C_t$ numbers of samples exposed to a plastic cuvette. Pre-treatment of the cuvette with carrier RNA or the addition of bovine serum albumin (BSA) to the buffer media may mitigate these issues. Amplification inhibition has been shown to frustrate interpretation and analysis of low copy DNA. Inhibition can lead to target underestimation, and ultimately to false negatives. An analysis of inhibition within our samples by serial dilution produced results shown in FIGS. 21A and 21B suggestive of inhibition within the lysis samples including variations in $\Delta C_t$ below what would be expected at 100% efficiency and increases in the detection of TREC episomal DNA in small dilutions of the lysis sample.

Figure 21A:
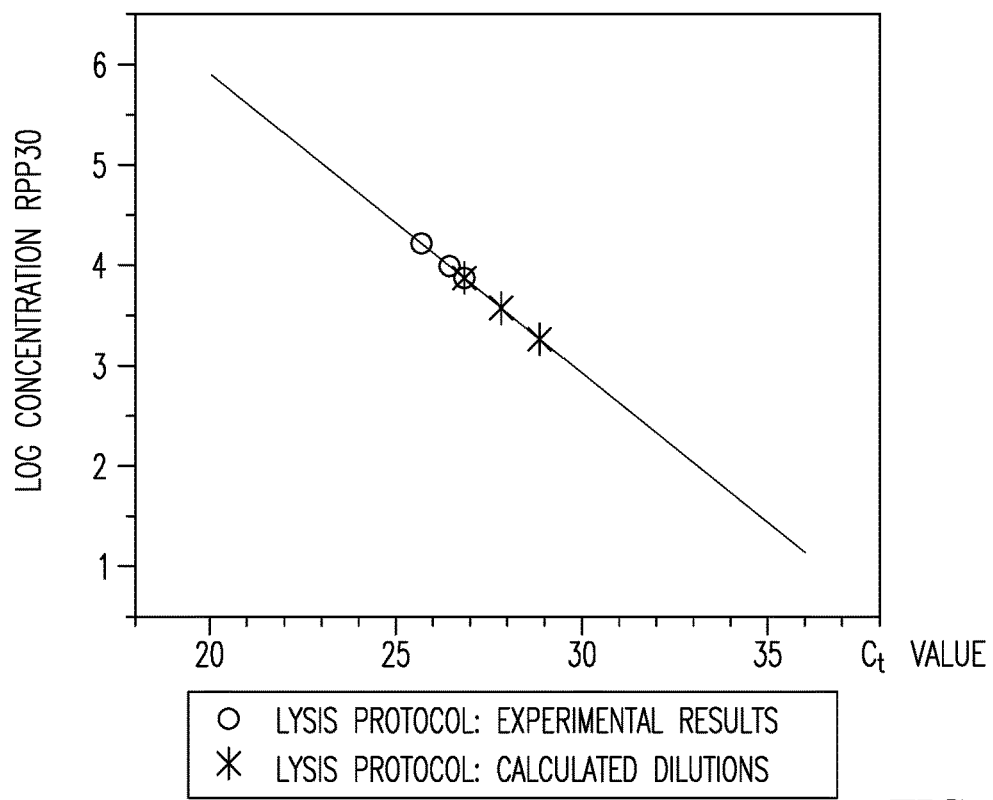
FIGS. 21A and 21B depict results of the experiments according to an example of the present technology.
Figure 21B:
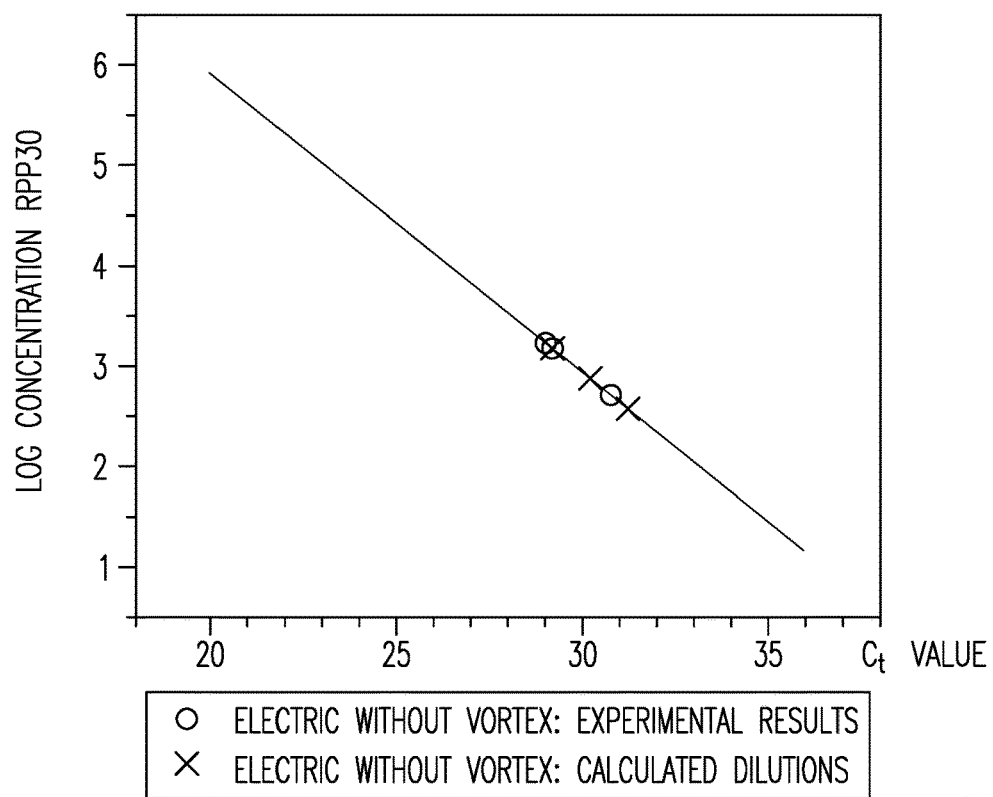

In particular, FIG. 21A illustrates results of 2-fold serial dilution of electric field extraction (without vortex) and FIG. 21B illustrates results of 2-fold serial dilution of the lysis procedure. Log concentrations of 2- and 4-fold dilutions were calculated from $C_t$ values and compared to calculated log concentrations from $C_t$ values at 100% amplification efficiency. The results suggest inhibition was seen in a serial two-fold dilution series. A fivefold serial dilution series was initially attempted, but failed to yield quantifiable results for electric procedure DNA samples. The two-fold dilution series was created by mixing 10 μL of sample with 10 μL of diluent. This process was repeated three times. Inhibition was assessed from the measured $C_t$ (threshold) and compared to the expected $C_t$ at 100% efficiency. Results were considered suggestive of inhibition if the $\Delta C_t$ between dilutions was <1. Lysis samples showed $C_t$ values suggestive of inhibition with a $\Delta C_t$ of 0.7. Small dilutions in the lysis sample also lead to detection of TREC episomal DNA in samples that previously did not show amplification (no amplification (no dilution), Ct=37.27 (2.5 fold dilution)). These observations suggest inhibition in the sample may interfere with TREC plasmid detection. These results suggest that inhibition may cause target underestimation in not only the lysis samples, but in the electric samples where template reduction may have affected the dilutions. The procedures described herein may be used for the extraction and/or purification of genomic and/or episomal DNA, RNA, and/or proteins from DBS.

In some implementations, any of the systems for preparing biological samples using electric fields described herein can have a gap width between electrodes of 0.01 cm, 0.02 cm, 0.05 cm, 0.1 cm, 0.2 cm, 0.5 cm, or 1.0 cm, and/or that is greater than 0.01 cm, greater than 0.02 cm, greater than 0.05 cm, greater than 0.1 cm, greater than 0.2 cm, or greater than 0.5 cm, and/or that is less than 1.0 cm, less than 0.5 cm, less than 0.2 cm, less than 0.1 cm, less than 0.05 cm, or less than 0.02 cm. In some implementations, any of the systems for preparing biological samples using electric fields described herein can use a buffer solution including potassium hydroxide (KOH) at a concentration of 5 mM, 10 mM, 15 mM, or 20 mM, and/or that is greater than 5 mM, greater than 10 mM, or greater than 15 mM, and/or that is less than 20 mM, less than 15 mM, or less than 10 mM.

In some implementations, any of the systems for preparing biological samples using electric fields described herein can use a voltage of 10 V, 25 V, or 50 V, and/or that is greater than 10 V or greater than 25 V, and/or that is less than 50 V or less than 25 V. In some implementations, any of the systems for preparing biological samples using electric fields described herein can apply a voltage across its electrodes and create the electric field for a pulse length of 30 s, 60 s, or 300 s, and/or that is greater than 30 s or greater than 60 s, and/or that is less than 300 s or less than 60 s.

In some implementations, any of the systems for preparing biological samples using electric fields described herein can heat a DBS to 40° C., 50° C., 60° C., 70° C., or 80° C., and/or to greater than 40° C., greater than 50° C., greater than 60° C., or greater than 70° C., and/or to less than 80° C., less than 70° C., less than 60° C., or less than 50° C. In some implementations, any of the systems for preparing biological samples using electric fields described herein can heat a DBS to such temperatures for a period of time of 1 minute, 2 minutes, 3 minutes, 4 minutes, 5 minutes, or 6 minutes, and/or of greater than 1 minute, greater than 2 minutes, greater than 3 minutes, greater than 4 minutes, or greater than 5 minutes, and/or to less than 6 minutes, less than 5 minutes, less than 4 minutes, less than 3 minutes, or less than 2 minutes.

Although the technology has been described with reference to particular examples and arrangements of parts, features and the like, these are not intended to exhaust all possible examples, arrangements, or features, and indeed many other modifications and variations will be ascertainable to those of skill in the art. U.S. provisional patent application No. 62/773,927, filed Nov. 30, 2018, to which this application claims priority, is hereby incorporated herein by reference, in its entirety. The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for separating bioanalytes from a substrate comprising a biological sample, comprising the steps of:
submerging at least a portion of the substrate containing the biological sample in a buffer solution, wherein the biological sample is blood and the substrate is a filter paper, the substrate having an end face spotted with the biological sample and a side surface joined to the end face;
bringing a first elongated electrical conductor into contact with the buffer solution, wherein the first elongated electrical conductor is a positive electrode;
bringing a second elongated electrical conductor into contact with the buffer solution, wherein the second elongated electrical conductor is a negative electrode, the side surface of the substrate faces at least one of the first elongated electrical conductor and the second elongated electrical conductor, and the end face of the substrate spotted with the biological sample faces a direction that is perpendicular to a side surface of at least one of the first and second elongated electrical conductors;
creating a difference in electric potential energy between the first and second elongated electrical conductors; and
collecting separated bioanalytes from at least one of the first and second elongated electrical conductors.

2. The method of claim 1, further comprising the step of:
positioning the portion of the substrate between the first and second elongated electrical conductors, including the side surface of the substrate facing both the first and second elongated electrical conductors.

3. The method of claim 2, wherein the step of creating a difference in electric potential energy between the first and second elongated electrical conductors comprises applying a voltage in a circuit connected to the first and second elongated electrical conductors such that the first elongated electrical conductor has an electrical charge and the second elongated electrical conductor has an opposite electrical charge.

4. The method of claim 3, wherein the step of applying a voltage comprises the steps of:
identifying a first type of bioanalyte to be removed from the substrate and collected;
determining a first amount of voltage and a first period of time, wherein at least one of the first amount of voltage and the first period of time is determined based at least in part on the first type of bioanalyte identified;
applying the determined first amount of voltage to the first elongated electrical conductor for the determined first period of time; and
collecting the first type of bioanalyte from at least one of the first and second elongated electrical conductors.

5. The method of claim 4, wherein the step of applying a voltage further comprises the steps of:
- identifying a second type of bioanalyte material to be removed from the substrate and collected, the second type being different than the first type to be collected;
- determining a second amount of voltage and a second period of time, wherein at least one of the second amount of voltage and the second period of time is determined based at least in part on the second type of bioanalyte material identified,
- wherein the second amount of voltage is different than the first amount of voltage, or the second period of time is different than the first amount of time, or both;
- applying the determined second amount of voltage to the first elongated electrical conductor for the determined second period of time; and
- collecting the second type of bioanalyte from at least one of the first and second elongated electrical conductors.

6. The method of claim 3, wherein at least one of the voltage applied and a period of time over which the voltage is applied is adjustable.

7. The method of claim 1, wherein the bioanalytes are nucleic acids.

8. The method of claim 7, wherein the nucleic acids are DNA molecules.

9. The method of claim 1, wherein the step of collecting separated bioanalytes further comprises the steps of:
- removing the first elongated electrical conductor from the buffer solution;
- inserting the first elongated electrical conductor into a material collection container; and
- reducing or eliminating the difference in electric potential energy between the first and second elongated electrical conductors.

10. The method of claim 1, wherein the step of collecting separated bioanalytes further comprises the steps of:
- removing the second elongated electrical conductor from the buffer solution;
- removing the portion of the substrate from the buffer solution; and
- reducing or eliminating the difference in electric potential energy between the first and second elongated electrical conductors.

11. The method of claim 1, wherein the step of collecting separated bioanalytes further comprises changing the buffer solution to a second buffer solution of different pH.

12. The method of claim 1, wherein the step of collecting separated bioanalytes further comprises changing the buffer solution to a second buffer solution of different salt concentration.

13. The method of claim 1, further comprising treating a container holding the buffer solution with carrier RNA prior to filling the container with the buffer solution.

14. The method of claim 1, further comprising adding bovine serum albumin to the buffer solution.

15. The method of claim 1, wherein a width of a gap between the first elongated electrical conductor and the second elongated electrical conductor is greater than 0.05 cm and less than 0.2 cm.

16. The method of claim 1, wherein the buffer solution includes potassium hydroxide at a concentration greater than 5 mM and less than 20 mM.

17. The method of claim 1, wherein creating a difference in electric potential energy between the first and second elongated electrical conductors includes creating a voltage of greater than 10 V and less than 50 V.

18. The method of claim 1, wherein creating a difference in electric potential energy between the first and second elongated electrical conductors includes creating a difference in electric potential energy between the first and second elongated electrical conductors for a period of time that is greater than 30 seconds and less than 300 seconds.

19. The method of claim 1, further comprising heating the substrate to a temperature greater than 40° C. and less than 80° C.

20. The method of claim 19, wherein heating the substrate includes heating the substrate for a period of time greater than one minute and less than six minutes.

21. The method of claim 1, wherein at least one of the first elongated electrical conductor and the second elongated electrical conductor terminates in a pointed tip.

22. A method for separating bioanalytes from a substrate comprising a biological sample, comprising the steps of:
- submerging at least a portion of the substrate containing the biological sample in a buffer solution, wherein the biological sample is blood and the substrate is a filter paper;
- contacting the buffer solution with a first elongated electrical conductor and a second elongated electrical conductor, wherein the first elongated electrical conductor is a positive electrode, the second elongated electrical conductor is a negative electrode, and at least one of the positive electrode and the negative electrode terminate in a pointed tip, wherein the substrate has an end face spotted with the biological sample and a side surface joined to the end face, the side surface of the substrate faces at least one of the positive electrode and the negative electrode, and the end face spotted with the biological sample faces a direction that is perpendicular to a side surface of at least one of the positive electrode and the negative electrode;
- identifying a first type of bioanalyte to be collected;
- determining a first amount of voltage and a first period of time, wherein at least one of the first amount of voltage and the first period of time is determined based at least in part on the first type of bioanalyte identified; and
- applying the determined first amount of voltage to the first elongated electrical conductor for the determined first period of time.

23. The method of claim 22, further comprising the steps of:
- identifying a second type of bioanalyte to be collected, the second type of bioanalyte to be collected being different than the first type of bioanalyte to be collected;
- determining a second amount of voltage and a second period of time, wherein at least one of the second amount of voltage and the second period of time is determined based at least in part on the second type of bioanalyte identified,
- wherein the second amount of voltage is different than the first amount of voltage, or the second period of time is different than the first amount of time, or both; and
- applying the determined second amount of voltage to the first elongated electrical conductor for the determined second period of time.

24. The method of claim 23, wherein either one or both of the first amount of difference in electric potential energy or the first period of time is selected to attract DNA to the first elongated electrical conductor; and
- wherein either one or both of the second amount of difference in electric potential energy or the second period of time is selected to attract RNA to the first elongated electrical conductor.

25. The method of claim 24, further comprising the steps of:
removing the first elongated electrical conductor from the buffer solution;
inserting the first elongated electrical conductor into a material collection container; and
reducing or eliminating the difference in electric potential energy between the first and second elongated electrical conductors.

26. The method of claim 22, further comprising the steps of:
removing the second elongated electrical conductor from the buffer solution;
removing the portion of the substrate from the buffer solution; and
reducing or eliminating the difference in electric potential energy between the first and second elongated electrical conductors.

27. A system for separating bioanalytes, comprising:
a substrate including an end face and a side surface joined to the end face, wherein the end face is spotted with a biological sample and the biological sample is blood and the substrate is a filter paper;
a first elongated electrical conductor;
a second elongated electrical conductor;
a process chamber containing buffer solution, wherein the substrate containing the biological sample is submerged in the buffer solution, and the first and second elongated electrical conductors are arranged in the buffer solution of the process chamber such that the substrate is disposed between the first and second elongated electrical conductors, and wherein the side surface of the substrate faces at least one of the first and second elongated electrical conductors and the end face of the substrate spotted with the biological sample faces a direction that is perpendicular to a side surface of at least one of the first and second elongated electrical conductors;
a source of electric power coupled to the first and second elongated electrical conductors for creating a difference in electrical potential energy between the first and second elongated electrical conductors;
at least one processor;
at least one computer-readable medium;
software stored in the computer-readable medium and programmed to execute on the at least one processor, wherein the software:
controls the source of electric power to apply a voltage in a circuit connected to the first and second elongated electrical conductors so that the first elongated electrical conductor has a positive charge and the second elongated electrical conductor has a negative charge; and
controls the source of electric power to reduce or eliminate the applied voltage so that material separated from the portion of a substrate can be collected from the first elongated electrical conductor.

28. The system of claim 27, further comprising:
a material collection chamber; and
a motor coupled to the first elongated electrical conductor and adapted to move the first elongated electrical conductor into and out of the process chamber;
wherein the software:
controls the motor to move the first elongated electrical conductor out of the process chamber and into the material collection chamber before the applied voltage is reduced or eliminated.

29. The system of claim 27, further comprising
a motor coupled to the second elongated electrical conductor and adapted to move the second elongated electrical conductor into and out of the process chamber; and
a sample removal device adapted to remove the portion of a substrate from the process chamber
wherein the software:
controls the motor to move the second elongated electrical conductor out of the process chamber before the applied voltage is reduced or eliminated; and
controls the sample removal device to remove the substrate from the process chamber before the applied voltage is reduced or eliminated.

30. The system of claim 27, further comprising that the software:
controls the source of electric power to apply a first amount of voltage in the circuit connected to the first and second elongated electrical conductors for a first period of time in order to attract a first component of the biological sample to the first elongated electrical conductor; and
controls the source of electric power to apply a second amount of voltage in the circuit connected to the first and second elongated electrical conductors for a second period of time in order to attract a second component of the biological sample to the first elongated electrical conductor;
wherein the second amount of voltage is different than the first amount of voltage or the second period of time is different than the first amount of time, or both.

31. The system of claim 27, wherein the process chamber and the first and second elongated electrical conductors are joined to form an electroporation cuvette, and at least one of the first and second elongated electrical conductors includes a pointed tip.

* * * * *